(12) United States Patent
Lee et al.

(10) Patent No.: US 10,538,747 B2
(45) Date of Patent: Jan. 21, 2020

(54) TRANSAMINASES AND METHOD, FOR DEAMINATING AMINO COMPOUND, USING SAME

(71) Applicant: CJ CHEILJEDANG CORPORATION, Seoul (KR)

(72) Inventors: Jae Hun Lee, Seoul (KR); Young Lyeol Yang, Seoul (KR); In Seok Oh, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/740,666

(22) PCT Filed: Jun. 3, 2016

(86) PCT No.: PCT/KR2016/005870
§ 371 (c)(1),
(2) Date: Dec. 28, 2017

(87) PCT Pub. No.: WO2017/003104
PCT Pub. Date: Jan. 5, 2017

(65) Prior Publication Data
US 2019/0032030 A1 Jan. 31, 2019

(30) Foreign Application Priority Data
Jul. 2, 2015 (KR) ........................ 10-2015-0094943

(51) Int. Cl.
C12P 13/00 (2006.01)
C12N 9/10 (2006.01)
C12P 13/14 (2006.01)

(52) U.S. Cl.
CPC ............ *C12N 9/1096* (2013.01); *C12P 13/14* (2013.01)

(58) Field of Classification Search
CPC .............................................. C12Y 206/01011
USPC ....................................................... 435/193
See application file for complete search history.

(56) References Cited

U.S. PATENT DOCUMENTS

| 2006/0003411 A1 | 1/2006 | Sugiyama et al. |
| 2014/0234916 A1 | 8/2014 | Takakura et al. |

FOREIGN PATENT DOCUMENTS

| JP | 2003159075 A | 6/2003 |
| KR | 101998050070 A | 9/1998 |
| KR | 1019990039948 A | 6/1999 |
| KR | 1020140128174 A | 11/2014 |
| WO | 2009113855 A2 | 9/2009 |
| WO | 2012050125 A1 | 4/2012 |
| WO | 20147197941 A1 | 12/2014 |

OTHER PUBLICATIONS

Accession No. (AC) S6JJQ1, Oct. 16, 2013 (Year: 2013).*
Database UniProt (entry version May 27, 2015) Accession No. S6JJQ1, Acetylornithine aminotransferase.
Extended European Search Report dated Nov. 13, 2018, of the European patent Application No. 16818137.8.
NCBI, GenBank Accession No. WP 017245727.1, Jun. 27, 2013.
Russian Office Action dated Dec. 4, 2018, of the Russian Patent Application No. 2018101961, with English Translation.
J.P. Vandecasteele, et al., "Aldehyde Dehydrogenases from Pseudomonas aeruginosa", Methods in Enzymology, 1982, vol. 89, pp. 484-490.
Luc Guerrillot, et al., "Purification and Characterization of Two Aldehyde Dehydrogenases from Pseudomonas aeruginosa" Eur. J. Biochem. 81, 185-192 (1977).
NCBI, GenBank Accession No. WP 048329493.1, Jun. 26, 2015.
V. Rajaram, et al., "Structure of biosynthetic N-acetylornithine aminotransferase from *Salmonella typhimurium*: Studies on Substrate specificity and inhibitor binding", Proteins 2008, 70, 429-441.
International Search report for PCT/KR2016/005870, dated Sep. 9, 2016 (4 pages with translation).
Database UniProtKB/TrEMBL [online], Accession No. A4XWF0, uploaded Apr. 1, 2015, [retrieved on Jan. 21, 2019].
Database UniProtKB/TrEMBL [online], Accession No. A5W0D2, uploaded May 27, 2015, [retrieved on Jan. 21, 2019].
Database UniProtKB/TrEMBL [online], Accession No. I7AZT5, uploaded May 27, 2015, [retrieved on Jan. 21, 2019].
Database UniProtKB/TrEMBL [online], Accession No. Q4ZQH5, uploaded Apr. 29, 2015, [retrieved on Jan. 21, 2019].
Database UniProtKB/TrEMBL [online], Accession No. S6BL00, uploaded Apr. 1, 2015, [retrieved on Jan. 21, 2019].
Database UniProtKB/TrEMBL [online], Accession No. S6JJQ1, uploaded May 27, 2015, [retrieved on Jan. 21, 2019].
Office Action dated Feb. 12, 2019, of the Japanese Patent Application No. 2017567772, with English Translation.

* cited by examiner

*Primary Examiner* — Tekchand Saidha
(74) *Attorney, Agent, or Firm* — Cantor Colburn LLP

(57) ABSTRACT

Provided are a novel separated polypeptide having transaminase activity, a polynucleotide encoding the polypeptide, a microorganism including the polynucleotide, and a method of deaminating an amino compound by using the polypeptide or the microorganism.

2 Claims, 17 Drawing Sheets
Specification includes a Sequence Listing.

FIG. 6

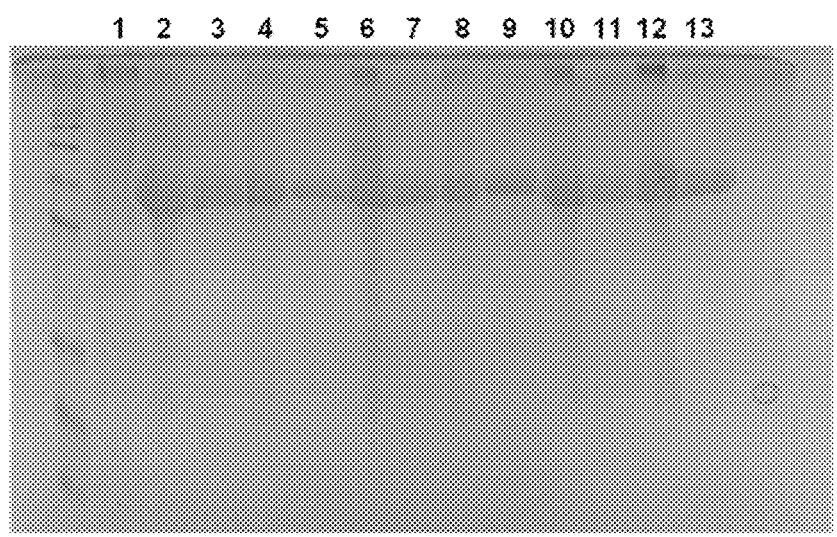

1. *E.coli* with pETDuet
2. Overexpression of *P. mendocina* N-acetylornithine transaminase (soluble proteins)
3. His-tag purified *P. mendocina* N-acetylornithine transaminase
4. Overexpression of *P. putida* N-acetylornithine transaminase (soluble proteins)
5. His-tag purified *P. putida* N-acetylornithine transaminase
6. Overexpression of *P. resinovorans* N-acetylornithine transaminase (soluble proteins)
7. His-tag purified *P. resinovorans* N-acetylornithine transaminase
8. Overexpression of *P. stutzeri* CJ-MKB transaminase (soluble proteins)
9. His-tag purified *P. stutzeri* CJ-MKB transaminase
10. Overexpression of *P. syringae* N-acetylornithine transaminase (soluble proteins)
11. His-tag purified *P. syringae* N-acetylornithine transaminase
12. Overexpression of *P. thermotolerans* N-acetylornithine transaminase (soluble proteins)
13. His-tag purified *P. thermotolerans* N-acetylornithine transaminase

TRANSAMINASES AND METHOD, FOR DEAMINATING AMINO COMPOUND, USING SAME

This application is a National Stage application of International Application No. PCT/KR2016/005870, filed Jun. 3, 2016, which claims the benefit of Korean Patent Application No. 10-2015-0094943 filed on Jul. 2, 2015, each of which is incorporated by reference in its entirety herein.

TECHNICAL FIELD

The present disclosure relates to a novel separated polypeptide having transaminase activity, a polynucleotide encoding the polypeptide, a microorganism including the polynucleotide, and a method of deaminating an amino compound by using the polypeptide or the microorganism.

BACKGROUND ART

Adipic acid is a dicarboxylic acidic compound having a molecular formula of $(CH_2)_4(COOH)_2$. Adipic acid has been widely used as a raw material for nylon resin, plastic plasticizers, and dyes and pharmaceuticals. In particular, as an important intermediate product for the production of a polyamide, such as nylon 6,6, adipic acid has a very high commercial value.

Adipic acid is mainly produced by a chemical method involving a two-step process using a petroleum compound as a raw material. In detail, cyclic compounds, such as phenol, cyclohexane, cyclohexene, and benzene, are used as starting materials and converted to ketone-alcohol oil (KA oil) named cyclohexanone or cyclohexanol. Then, through an oxidation process using nitric acid, adipic acid is produced. Such a chemical process is highly efficient and economical, but use of benzene as a raw material and the production of an enormous amount of nitrogen oxide as a by-product are considered to be problems. In addition to these problems, due to environmental regulations that have recently been strengthened, the need for environmentally friendly processes for the production of adipic acid has emerged. In this regard, efforts to produce adipic acid through microorganisms are about to begin. However, a biosynthesis or biodegradation pathway of 6-aminocaproic acid, which can be used as an intermediate for the production of adipic acid, is not accurately known yet. If a 6-amine group of 6-aminocaproic acid is removed and a ketone group is introduced thereto, adipate semialdehyde is produced, and through an aldehyde dehydrogenase reaction, it is expected that the synthesis of adipic acid is possible (Guerrillot L. et al., Eur J Biochem., 1977, 81(1):185-92; Vandecasteele, J. P. et al., Methods Enzymol., 1982, 89: 484-490). The enzymatic conversion reaction from 6-aminocaproic acid to adipic acid, which consists of the same number of carbons as 6-aminocaproic acid, is highly valued as a novel technology as well as for its high commercial value. However, an enzyme or a microorganism that can participate in the actual reaction is not known.

In this regard, the inventors of the present disclosure isolated a novel microorganism having deamination activity while studying the deamination of 6-aminocaproic acid, and accordingly, a novel enzyme has been discovered from the novel microorganism, thereby completing the present disclosure.

DETAILED DESCRIPTION OF THE INVENTION

Technical Problem

The present disclosure provides a novel separated polypeptide having transaminase activity.

The present disclosure provides a polynucleotide encoding the polypeptide.

The present disclosure provides a microorganism transformed to express the novel polypeptide.

The present disclosure provides a method of deaminating an amino compound, and a method of converting a semialdehyde compound to an amino compound by using the polypeptide having the transaminase activity.

Technical Solution

An aspect of the disclosure provides a separated polypeptide having transaminase activity, the polypeptide having an amino acid sequence of SEQ ID NO: 7 or an amino acid sequence having at least 75% homology with SEQ ID NO: 7.

The term "polypeptide having transaminase activity" as used herein refers to a polypeptide having activity of catalyzing a reversible amino group transfer reaction between an amino acid and an α-keto acid. The transaminase may be named aminotransferase.

The term "polypeptide" as used herein refers to a polymer of amino acids. In general, a form where a few amino acids are linked together is called a peptide, and a form where many amino acids are linked together is called a protein. About 20 types of amino acids, which constitute a protein, are linked to each other via chemical bonding to form a polypeptide. The polypeptide having transaminase activity of the present disclosure may include an amino acid sequence of SEQ ID NO: 7. In addition, as an amino acid sequence having at least 75%, at least 80%, at least 90%, for example, at least 95%, and for example, at least 99% homology with SEQ ID NO: 7, the polypeptide may have any amino acid sequence without limitation, as long as an amino acid sequence of the polypeptide has activity of catalyzing an amino group transfer reaction of a transaminase. The amino acid sequence having at least 75%, at least 80%, at least 90%, for example, at least 95%, and for example, at least 99% homology with SEQ ID NO: 7, for example, comprises amino acid sequence of SEQ ID: 9, SEQ ID NO: 11, SEQ ID NO: 13, SEQ ID NO: 15, or SEQ ID NO: 17. In addition, as long as an amino acid sequence of the polypeptide is biologically equivalent to the polypeptide or has equivalent activity to the polypeptide, the polypeptide may include a variant or an analogue of the amino acid sequence.

The term "homology" as used herein refers to the degree of sequence identity with respect to a given polypeptide sequence or polynucleotide sequence, wherein the degree can be represented as a percentage. In the specification, homology of a sequence identical to a given polypeptide sequence or polynucleotide sequence or homology of a sequence having similar activity to that of a given polypeptide sequence or polynucleotide sequence is represented in terms of "% homology". For example, the homology may be determined by using standard software, e.g., BLAST 2.0, to calculate parameters, such as score, identity, and similarity. Alternatively, the homology may be identified by comparing sequences according to a hybridization method, such as southern hybridization, performed under defined stringent conditions. The defined and appropriate conditions for the hybridization method may be determined in consideration of methods well known to one of ordinary skill in the art.

The polypeptide having transaminase activity may be derived from *P. stutzeri*. In detail, the polypeptide may be derived from *P. stutzeri* CJ-MKB (KCCM11587P). In one embodiment, the inventors of the present disclosure separated or isolated *P. stutzeri* CJ-MKB, which is a novel strain that can fix 6-aminocaproic acid as a nitrogen source, thereby obtaining a novel transaminase.

The polypeptide having transaminase activity of the present disclosure may deaminate an amino compound. The amino compound may include at least one selected from the group consisting of N-acetylornithine, gamma-aminobutyric acid (4-aminobutyric acid), 5-aminovaleric acid, and 6-aminocaproic acid, but is not limited thereto. In detail, the amino compound may be 5-aminovaleric acid or 6-aminocaproic acid. A conventionally known N-acetylornithine transaminase is known to use N-acetylornithine and N-succinyl-L-2-amino-6-oxopimelate as a substrate. However, it is not known at all whether gamma-aminobutyric acid, 5-aminovaleric acid, or 6-aminocaproic acid is used as a substrate (Rajaram V, Ratna Prasuna P, Savithri H S, Murthy M R. Structure of biosynthetic N-acetylornithine aminotransferase from Salmonella typhimurium: studies on substrate specificity and inhibitor binding, Proteins, 2008, 70(2):429-441). However, the polypeptide of the present disclosure may use, as a substrate, gamma-aminobutyric acid, 5-aminovaleric acid, or 6-aminocaproic acid, in addition to N-acetylornithine, to thereby catalyze a deamination reaction thereof. In one embodiment, N-acetylornithine, gamma-aminobutyric acid, 5-aminovaleric acid, or 6-aminocaproic acid can be deaminated by the polypeptide of the present disclosure, and the production of glutamate can be confirmed.

Another aspect of the present disclosure provides a polynucleotide encoding the polypeptide having transaminase activity.

The term "polynucleotide" as used herein refers to a polymer of nucleotides in which nucleotide monomers are linked in a long chain via covalent bonds, and in general, refers to a deoxyribonucleic acid (DNA) strain or ribonucleic acid (RNA) strain of more than a certain length.

The polynucleotide may include a nucleotide sequence encoding a polypeptide of SEQ ID NO: 7 or a polypeptide having at least 75% homology with SEQ ID NO: 7. In detail, the polynucleotide may include a base sequence of SEQ ID NO: 4. In addition, the polynucleotide may include a sequence having at least 80%, for example, at least 90%, for example, at least 95% homology with SEQ ID NO: 4, as long as the sequence is a nucleotide sequence encoding the protein having transaminase activity according to the present disclosure. In addition, due to the degeneracy of the genetic code, the polynucleotide may include a variant of the nucleotide sequence encoding the same amino acid sequence.

Another aspect of the present disclosure provides a microorganism transformed to express the polypeptide having transaminase activity. In detail, the microorganism is transformed to express a polynucleotide encoding a polypeptide having transaminase activity, and more particularly, may be transformed by a recombinant vector to which the polynucleotide is operably linked.

The polypeptide and the polynucleotide are as described above, respectively.

The term "operably linked" as used herein means that the gene sequence is functionally linked to a promoter sequence that initiates and mediates the transcription of the polynucleotide encoding the polypeptide having transaminase activity according to the present disclosure. The linkage with the expression vector can be prepared using genetic recombination technology known in the art. For example, a site-specific DNA cleavage and linkage may be prepared using a nicking enzyme and a linking enzyme.

The term "expression vector: as used herein refers to a DNA construct including a base sequence of a polynucleotide that encodes a target protein, which is operably linked to a suitable control sequence so that the target protein can be expressed in a suitable host cell. The control sequence may include a promoter for initiating the transcription, any operator sequence for controlling the transcription, a sequence encoding a suitable ribosome binding site of mRNA, and a sequence for controlling the transcription and translation termination. The vector may be transformed into a suitable host, and then, replicated or functionalized, regardless of the host genome. In addition, the vector may be integrated into the host genome itself. The vector used in the present disclosure is not particularly limited as long as the vector is replicable in a host, and any vector known in the art may be used. Examples of the conventionally used vector are a natural or recombinant plasmid, a cosmid, a virus, and a bacteriophage, but are not limited thereto. When the expression vector including the polynucleotide encoding the polypeptide having the transaminase activity is transformed or transfected into a host cell, a desirable polypeptide having transaminase activity can be expressed in the host cell.

The term "transformation" as used herein refers to the introduction of a vector, which includes a target protein-coding polynucleotide, into a host cell to allow expression of a protein encoded by the polynucleotide in the host cell. As long as the expression is allowed in the host cell, the transformed polynucleotide may include all types in any case whether the transformed polynucleotide is inserted in the chromosomes of the host cell or the transformed polynucleotide is located outside the chromosomes of the host cell. The method of transforming the vector of the present disclosure into the cell includes any method of introducing a base into a cell, and for example, the transformation may be performed by selecting suitable standard techniques known in the art, such as electroporation, calcium phosphate co-precipitation, retroviral infection, microinjection, DEAE-dextran, a cationic liposome method, or like. However, the transformation method is not limited thereto.

The term "transformed microorganism" as used herein refers to any microorganism including both a prokaryotic microorganism and a eukaryotic microorganism, as long as a microorganism can express the polypeptide having transaminase activity. The microorganism may be a strand of a microorganism belonging to the genus *Escherichia, Erwinia, Serratia, Providencia, Corynebacterium*, or *Brevibacterium*. For example, the microorganism may belong to the genus *Escherichia*, and for example, may be *Eschericia coli*.

Another aspect of the present disclosure provides a method of deaminating an amino compound, the method including adding the polypeptide having transaminase activity or a microorganism expressing the polypeptide to a solution containing the amino compound.

Regarding the method, the polypeptide having transaminase activity is as described above.

Regarding the method, the microorganism expressing the polypeptide having transaminase activity may be transformed with a recombinant vector that includes a polynucleotide encoding the polypeptide having transaminase activity. Such a transformed microorganism is as described above. The microorganism may be added to the solution containing the amino compound in the form of a culture of the microorganism or a lysate of the microorganism.

The amino compound may include, for example, at least one selected from the group consisting of N-acetylornithine, gamma-aminobutyric acid, 5-aminovaleric acid, and 6-aminocaproic acid, but is not limited thereto. In addition, the amino compound may include, for example, gamma-aminobutyric acid, 5-aminovaleric acid, or 6-aminocaproic acid.

The solution containing the amino compound may include at least one selected from the group consisting of pyruvate, oxaloacetate, and α-ketoglutarate, in addition to pyridoxal phosphate. The pyridoxal phosphate may be required as a coenzyme in the transaminase reaction of the polypeptide of the present disclosure. In addition, the pyruvate, the oxaloacetate, and the α-ketoglutarate may be used as amine acceptors to accept an amino group that is released from the amino group in the reaction.

In addition, the method of deaminating the amino compound may further include recovering the compound from which the amino group is removed from the reaction product. The compound from which the amino group is removed may include at least one selected from the group consisting of N-acetylglutamate5-semialdehyde, succinate semialdehyde, glutarate semialdehyde, and adipate semialdehyde, but is not limited thereto. Regarding the method of recovering a compound from which the amino group is removed from a cell or a culture, depending on a culturing method, a compound from which the amino group is removed is collected or recovered from the culture using a suitable method known in the art. For example, centrifugation, filtration, anion exchange chromatography, crystallization, and HPLC may be used, but embodiments are not limited thereto.

Another aspect of the present disclosure provides a method of producing an amino compound, the method including adding a polypeptide having transaminase activity or the microorganism expressing the polypeptide to a solution containing a semialdehyde compound.

Regarding the method of producing the amino compound, the polypeptide having transaminase activity is as described above. The polypeptide having transaminase activity also has catalytic activity for a reverse reaction of the deamination of the amino compound, such that a semialdehyde compound can be converted to an amino compound. The semialdehyde compound may include at least one selected from the group consisting of N-acetylglutamate 5-semialdehyde, succinate semialdehyde, glutarate semialdehyde, and adipate semialdehyde, but is not limited thereto. Regarding the method of producing the amino compound, the solution containing the semialdehyde compound may further include glutamate or aspartate, in addition to pyridoxal phosphate.

In addition, the method of producing the amino compound may further include recovering the produced amino compound from the solution. The amino compound may include at least one selected from the group consisting of N-acetylornithine, gamma-aminobutyric acid, 5-aminovaleric acid, and 6-aminocaproic acid, but is not limited thereto. The recovering of the produced amino compound may be performed by a suitable method known in the art.

The method of deaminating the amino compound may be used for the production of adipic acid. Regarding the method of producing adipic acid, the transaminase of the present disclosure or a lysate of the microorganism including the transaminase may be added to a solution containing 6-aminocaproic acid as the amino compound, and then, adipic acid may be synthesized from adipate semialdehyde that is converted from the 6-aminocaproic acid by using a suitable method known in the art. The synthesis of adipic acid from the adipate semialdehyde may be preferably performed by an aldehyde dehydrogenase reaction.

Advantageous Effects of the Invention

The polypeptide having transaminase activity of the present disclosure was first discovered. In addition, the method of deaminating the amino compound by using the polypeptide can be applied to a bio-based production method of adipic acid. That is, in consideration of the production of adipic acid using a conventional chemical method, the present disclosure is meaningful in terms of providing the basis for bio-based production of adipic acid using a novel path.

In detail, it shows the resultant obtained by culturing a single colony and performing centrifugation thereon, and illustrates separation of the resultant into the bio-film and the strain by using distilled water.

FIGS. 2A to 2F show the results of a comparison of the production of glutamate and the degree of substrate degradation on TLC, depending on various concentrations of 5-aminovaleric acid, 6-aminocaproic acid, alpha-ketoglutaric acid, and pyridoxal phosphate and the presence and absence of each substrate:

[5AVA: 10 mM 5-aminovaleric acid (standard); 1: 20 mM 6-aminocaproic acid (standard); 2: *P. stutzeri* CJ-MKB+20 mM 6-aminocaproic acid; 3: *P. stutzeri* CJ-MKB+10 mM 6-aminocaproic acid, and 20 mM 5-aminovaleric acid; 4: *P. stutzeri* CJ-MKB+20 mM 6-aminocaproic acid, 10 mM alpha-ketoglutarate, and 0.1 mM pyridoxal-phosphate; 4-1: *P. stutzeri* CJ-MKB+20 mM 6-aminocaproic acid, and 10 mM alpha-ketoglutarate; 5: *P. stutzeri* CJ-MKB+10 mM 6-aminocaproic acid, 20 mM 5-aminovaleric acid, 10 mM alpha-ketoglutarate, and 0.1 mM pyridoxal-phosphate; 5-1: *P. stutzeri* CJ-MKB+10 mM 6-aminocaproic acid, 20 mM 5-aminovaleric acid, and 10 mM alpha-ketoglutarate; 6: *P. stutzeri* CJ-MKB+20 mM 6-aminocaproic acid, and 20 mM glutamate; E: 10 mM glutamate (standard)].

Figure 3:
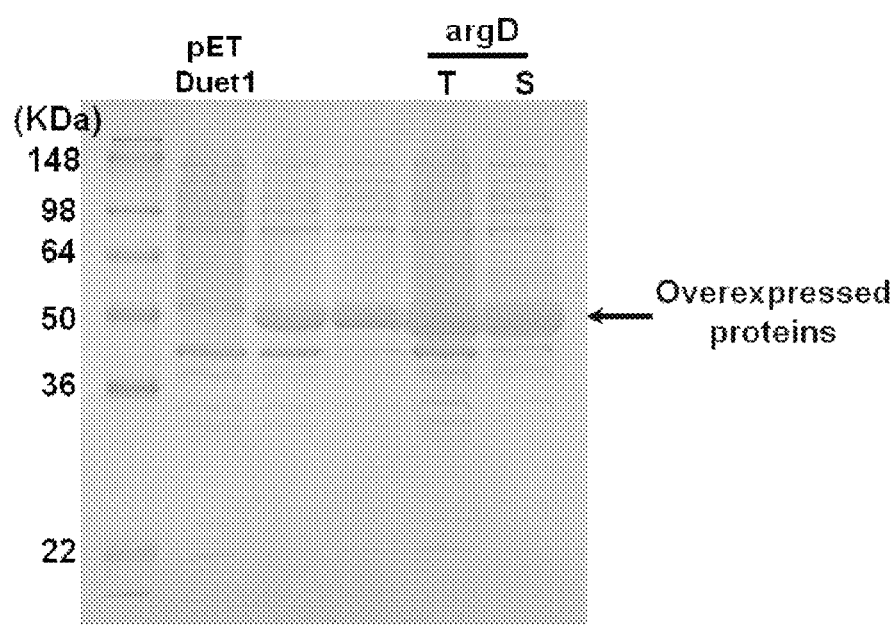

FIG. 3 is an SDS-PAGE image showing that soluble proteins are overexpressed in *E. coli* transformed with genes of the polypeptide having transaminase activity of the present disclosure:

[T: cell lysate; S: soluble protein].

Figure 4:
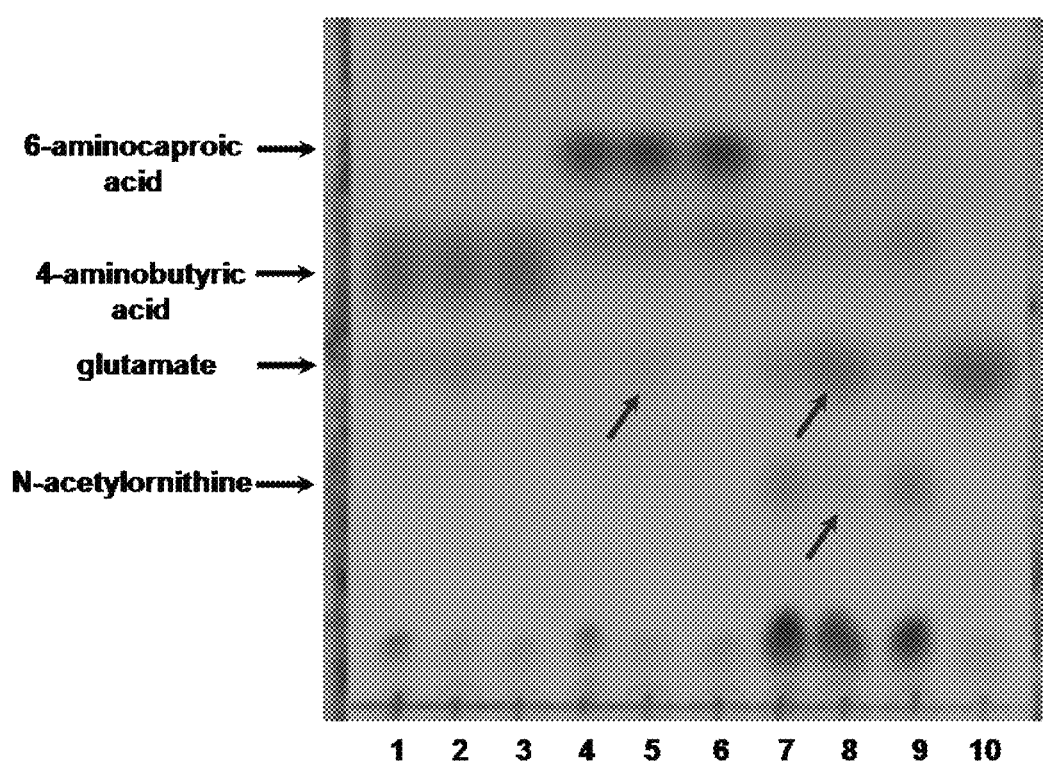

FIG. 4 shows TLC results for the reactivity to amino compounds by using the cell lysate of *E. coli* in which the polypeptide having transaminase activity of the present disclosure is overexpressed:

[1: reaction between overexpressed pETDuet1 (empty vector) and 4-aminobutyric acid; 2: reaction between overexpressed polypeptide having transaminase activity of the present disclosure and 4-aminobutyric acid; 4: reaction between overexpressed pETDuet1 and 6-aminocaproic acid; 5: reaction between overexpressed polypeptide having transaminase activity of the present disclosure and 6-aminocaproic acid; 7: reaction between overexpressed pETDuet1 and N-acetylornithine; 8: reaction between overexpressed polypeptide having transaminase activity of the present disclosure and N-acetylornithine; and 10: glutamate (standard)].

Figure 5:
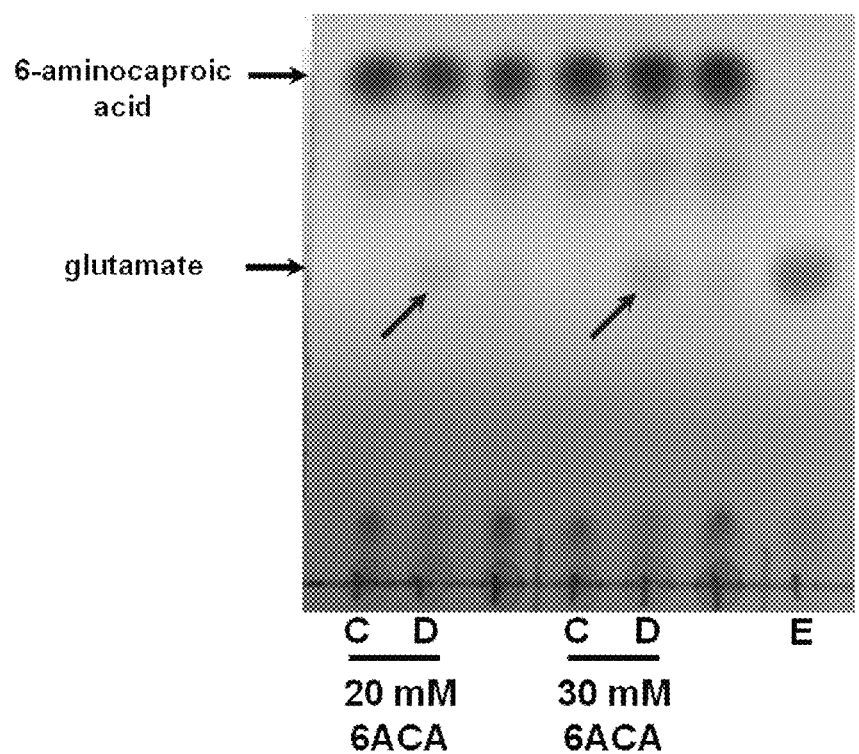

FIG. 5 shows TLC results showing the amount of glutamate produced by a conversion reaction using the polypeptide having transaminase activity of the present disclosure by increasing the concentration of 6-aminocaproic acid:

[C: reaction between overexpressed pETDuet1 and 6-aminocaproic acid; D: reaction between overexpressed polypeptide having transaminase activity of the present disclosure and 6-aminocaproic acid, and E: 10 mM glutamate (standard)].

FIG. 6 is an SDS-PAGE image showing results of overexpression of N-acetylornithine transaminases obtained from five *Pseudomonas* strains and the polypeptide having transaminase activity of the present disclosure, in *E. coli*.

Figure 7:
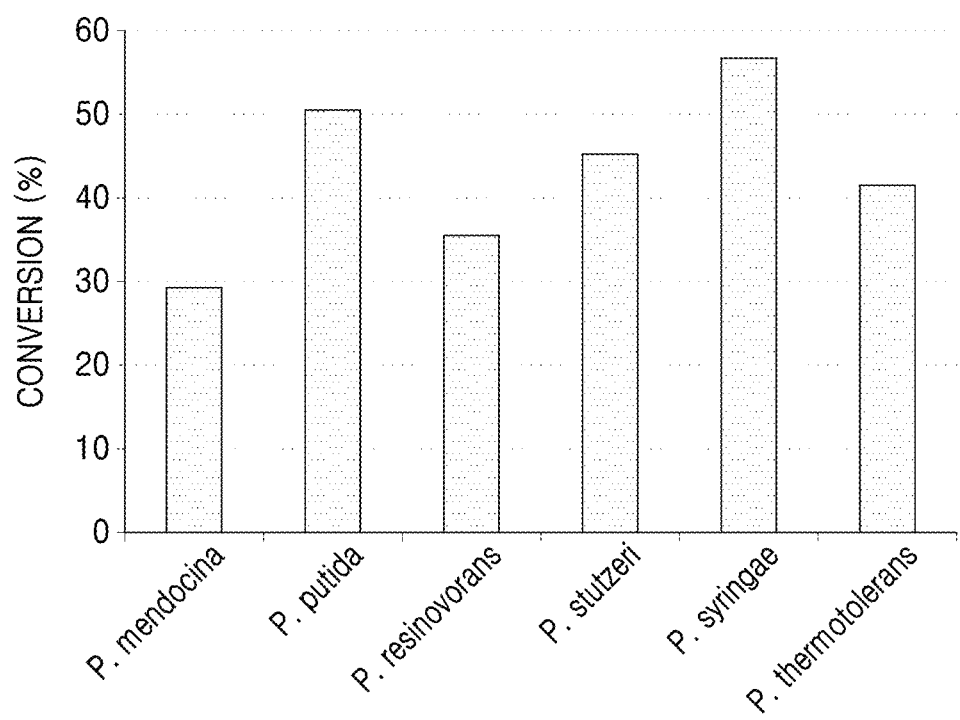

FIG. 7 is a graph showing results of analysis of the decrease of 6-aminocaproic acid using LC-MASS after a 1-hour reaction between 6-aminocaproic acid and the N-acetylornithine transaminases derived from the five *Pseudomonas* strains and the polypeptide having transaminase activity of the present disclosure.

Figure 8:
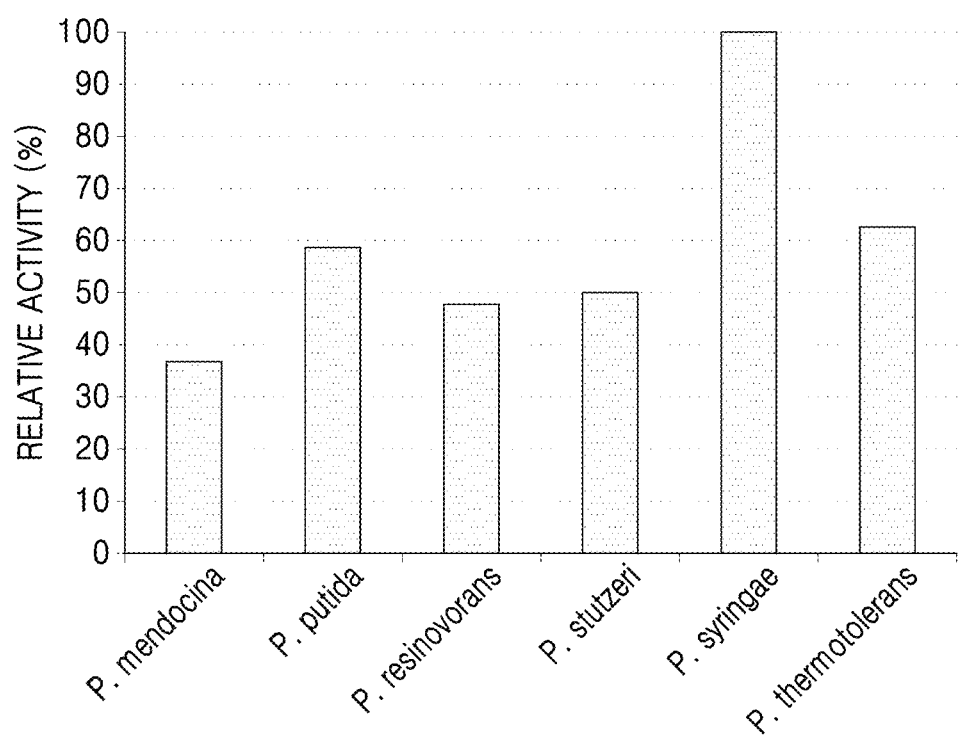

FIG. 8 shows the results of comparing the same samples as in FIG. 7 in terms of the degree of aldehyde formation according to a relative activity value from Schiff's reagent.

Figure 9:
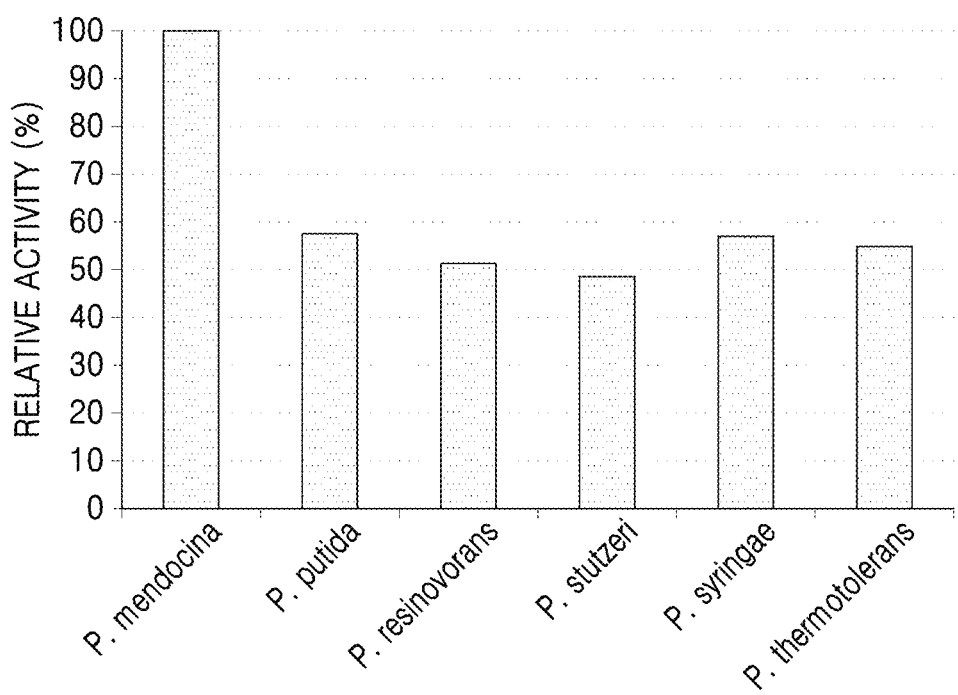

FIG. 9 is a graph showing analysis of the decrease of N-acetylornithine using LC-MASS after a reaction between N-acetylornithine and the N-acetylornithine transaminases derived from the five *Pseudomonas* strains and the polypeptide having transaminase activity of the present disclosure.

Figure 10:
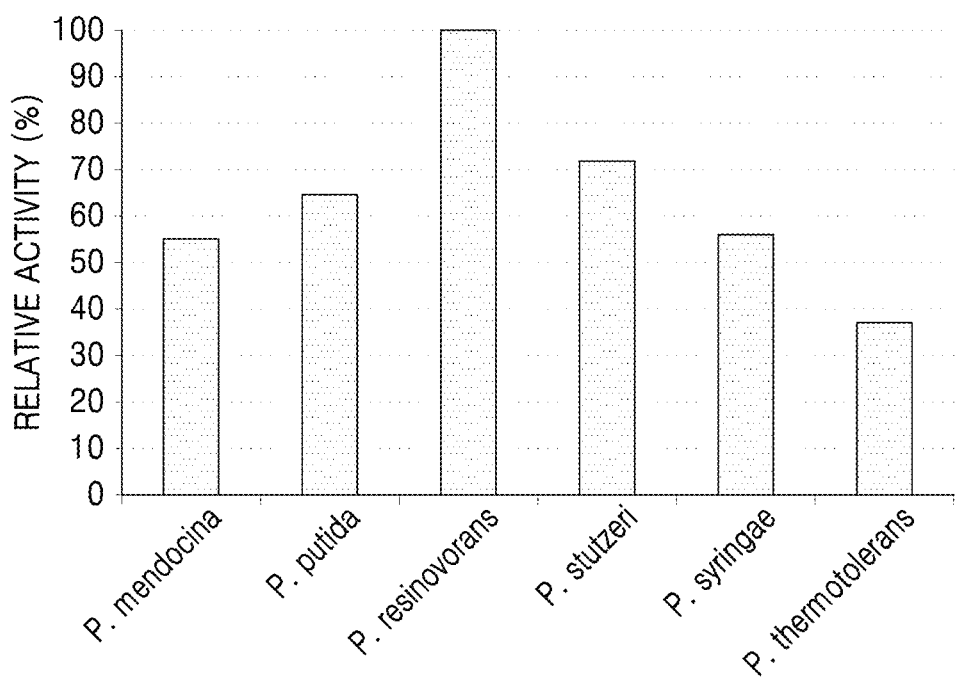

FIG. 10 is a graph showing analysis of the decrease of gamma-aminobutyric acid using LC-MASS after a reaction between gamma-aminobutyric acid and the N-acetylornithine transaminases derived from five *Pseudomonas* strains and the polypeptide having transaminase activity of the present disclosure.

Figure 11:
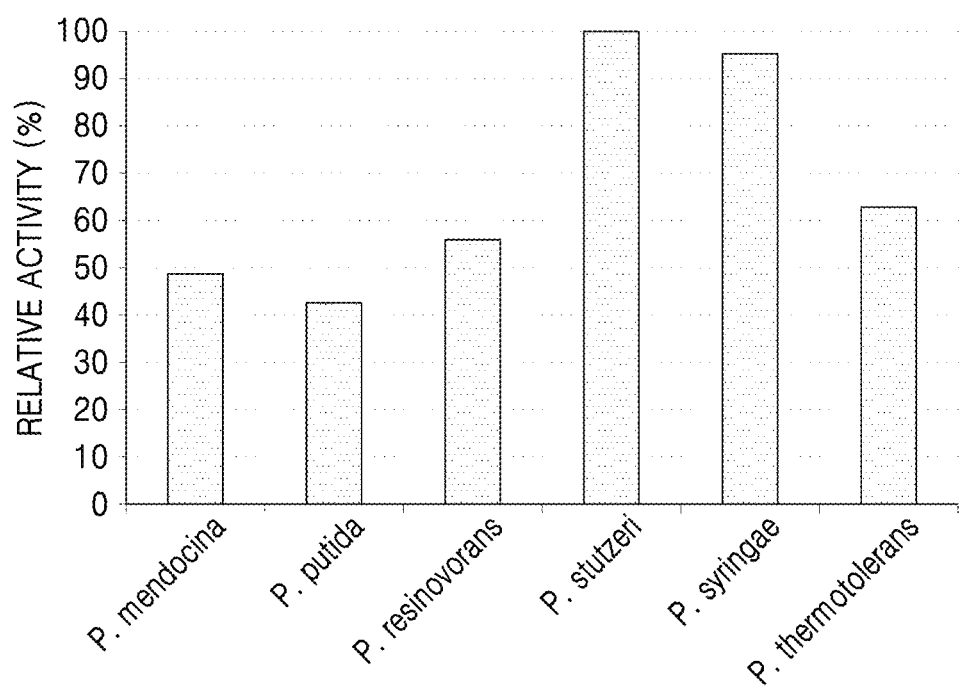

FIG. 11 is graph showing analysis of the decrease of 5-aminovaleric acid using LC-MASS after a reaction between 5-aminovaleric acid and the N-acetylornithine transaminases derived from the five *Pseudomonas* strains and the polypeptide having transaminase activity of the present disclosure.

Figure 12:
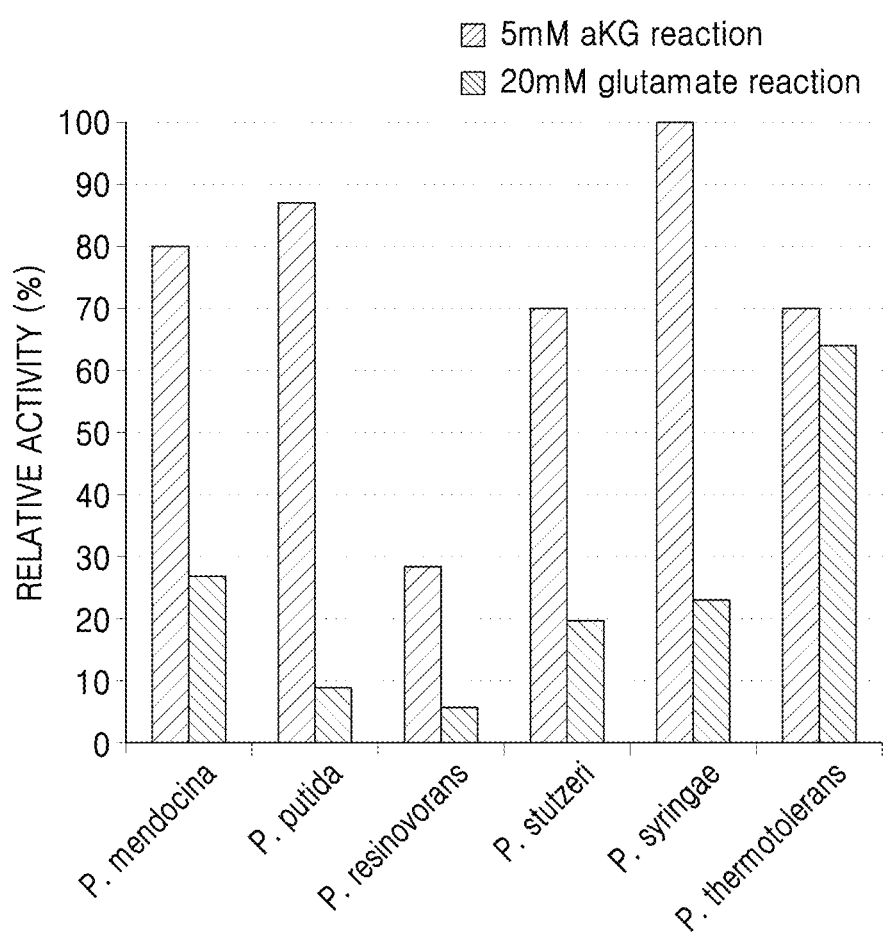

FIG. 12 is a graph showing results obtained by comparing the relative enzymatic activity through Schiff's reagent from a reaction with 6-aminocaproic acid and induction of a reverse reaction thereof again, to evaluate a reverse reaction of the polypeptide having transaminase activity of the present disclosure.

BEST MODE

Mode of the Invention

Hereinafter, one or more embodiments will be described in more detail with reference to the following examples. However, these examples are not intended to limit the scope of the present disclosure.

Example 1: Identification of a Microorganism using 6-aminocaproic Acid as a Nitrogen Source 1) Screening of a Microorganism using 6-aminocaproic Acid as a Nitrogen Source and Analysis of 16S rRNA 6-aminocaproic acid (6-ACA) was fixed as a nitrogen source, and a novel strain, *P. stutzeri* CJ-MKB, which can deaminate 6-ACA, was selected through a subculture. For the selection, a minimal medium in which a microorganism can be cultured was prepared with the composition of Table 1. Here, a nitrogen source for the strain culture was 6-ACA.

TABLE 1

| Medium composition | Final concentration |
|---|---|
| $Na_2HPO_4 \cdot H_2O$ | 15.1 mM |
| $KH_2PO_4$ | 22 mM |
| NaCl | 8.6 mM |
| 6-aminocaproic acid | 20 mM |
| $MgSO_4$ | 1 mM |
| $CaCl_2$ | 100 mM |
| $(NH_4)6MO_7O_{24} \cdot H_2O$ | 3 nM |
| $H_3BO_3$ | 400 nM |
| $CoCl_2 \cdot H_2O$ | 30 nM |
| $CuSo_4 \cdot H_2O$ | 10 nM |
| $MnCl_2 \cdot H_2O$ | 80 nM |
| $ZnSO_4 \cdot H_2O$ | 10 nM |
| $FeSO_4 \cdot H_2O$ | 1 mM |
| Glucose | 11.1 mM |

In detail, a soil sample from the Gimpo Plant of CJ Cheiljedang Corp., located in Gayang-dong, Seoul, Korea, was cultured in a medium having the composition of Table 1 at a temperature of 37° C. and at a speed of 200 rpm. The cultured candidate strains were cultured again until an optical density thereof reached 0.5 under the conditions where the same medium was used at an initial inoculation optical density (OD600) of 0.05, at a temperature of 37° C., and at a speed of 200 rpm. Then, a microorganism cultured in the medium having the composition of Table 1 was selected through a subculture five times. The selected microorganism was primarily named 'CJ-MKB', and the following experiment was performed to confirm that the selected microorganism was a new microorganism.

The CJ-MKB strains cultured in the liquid medium were streaked and spread over an M9 agar plate to obtain colonies. The colonies obtained therefrom were resistant to ampicillin at a concentration of 25 mg/ml. In addition, it was observed that a light-colored bio-film was formed around the colonies. Two colonies were selected and cultured again in the M9 liquid medium, and genomic DNA was extracted using a genomic DNA prep kit. To identify the obtained genome, 16S ribosomal RNA (16S rRNA) sequences were analyzed. Here, primers commonly used for analysis of the 16S rRNA sequences of the microorganism, such as 27F (AGA GTT TGA TCC TGG CTC AG; SEQ ID NO: 18) and 1492R (GGT TAC CTT GTT ACG ACT T; SEQ ID NO: 19), were used, and accordingly it was confirmed that the 16S rRNA of the CJ-MKB genome had a base sequence of SEQ ID NO: 1.

The BLAST program provided by the National Center for Biotechnology Information (NCBI) was used to search for a strain having high nucleic acid homology with SEQ ID NO: 1 (http://blast.ncbi.nlm.nih.gov/Blast.cgi° C. PROGRAM=blastn&PAGE_TYPE=Blast Search&LINK_LOC=blasthome). As a result, it was confirmed that the strain had the same sequence as 16S rRNA of each of *P. stutzeri* strain NBRIS11, gamma proteobacterium BP44-iso8, uncultured bacterium clone 9, *Escherichia coli* strain BM0446, and enterobacteriaceae bacterium BM005, respectively.

Figure 1:
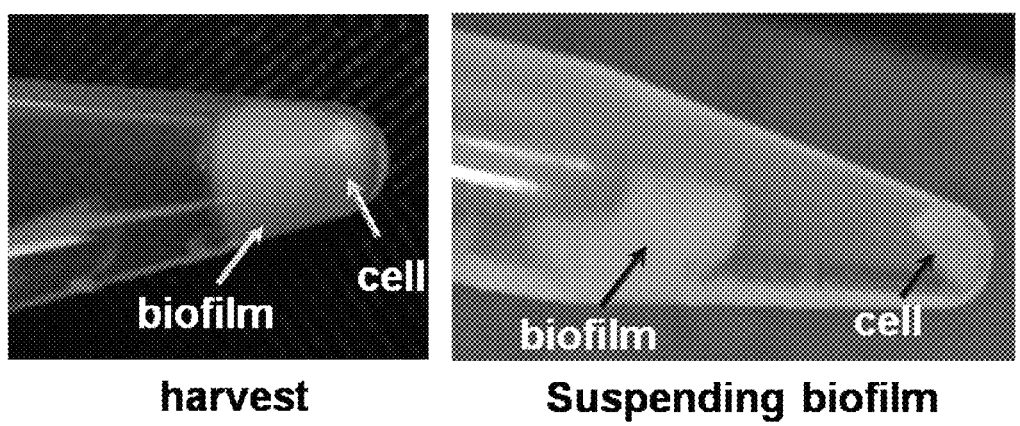
FIG. 1 is an image showing that a strain selected by using a minimal medium that includes 6-aminocaproic acid as a nitrogen source forms a bio-film.

Several microorganisms of the genus *Pseudomonas* are known to produce exopolysaccharide for the formation of a bio-film. In addition, the microorganisms of the genus *Pseudomonas* were also resistant to beta-lactam antibiotics, such as penicillin. In consideration of the sequence information of 16S rRNA of the CJ-MKB strain, the resistance to ampicillin, and the bio-film as shown during the culturing, the selected strain was highly expected to be a microorganism of the genus *Pseudomonas*. The single colony obtained on the M9 medium agar plate containing 25 mg/ml of ampicillin was cultured in an LB broth, and then centrifuged at a speed of 13,000 rpm for 1 minute, thereby obtaining a culture of the strain (FIG. 1). When distilled water was added to the obtained strain and the mixed solution was lightly shaken, the bio-film and the strain were easily separated from each other.

2) Sequence Analysis of Oxidoreductase

To determine whether the selected strain was a microorganism of the genus Pseudomonas, it was analyzed whether the novel CJ-MKB strain had a base sequence of an oxidoreductase that is present in the genus Pseudomonas. Here, newly designed primers, such as NCPPB 5P (ATGAGCAAGACTAACGAATCCC; SEQ ID NO: 20) and NCPPB 3P (TCCAGAATGGCCAGCCCGCG; SEQ ID NO: 21), were used to perform the sequence analysis. As a result, it was confirmed that the selected strain had a base sequence of SEQ ID NO: 2.

As a result of analysis using the BLAST problem of NCBI with respect to the base sequence of SEQ ID NO: 2, it was confirmed that the base sequence of SEQ ID NO: 2 has the same sequence as a molybdopterin-binding sequence of an oxidoreductase of the known P. stutzeri A1501 strain. In this regard, it was confirmed that selected novel CJ-MKB strain was a microorganism of the genus Pseudomonas.

3) Sequence Analysis of Transaminase

Since the nucleotide sequence confirmed to have homology is a short sequence of 714 bases, the subgrouping of the microorganism could not be classified correctly. In this regard, additional protein nucleic acid sequences were analyzed to confirm the subgrouping. When the microorganism used 6-ACA as a nitrogen source, N-ACETYLORNITHINE transaminase or 4-aminobutyrate transaminase, among transaminases, is specifically expected to be involved in an enzyme conversion reaction. Accordingly, the base sequence of the protein having the two enzymatic activities was confirmed.

In detail, for comparative analysis of the base sequences for N-acetylornithine transaminase that are present in the genomes of P. stutzeri A1501 and the selected CJ-MKB strain, argD_F2 (5' primer: ATTTAAGGATCCGTCCGCCCCGCACACCCCGG; SEQ ID NO: 22) and argD_R2 (3' primer: ATTTAAGAGCTCTCAGGCCTGGGTCAGCGTC; SEQ ID NO: 23) were used to analyze the nucleic acid sequences by PCR. As a result, it was confirmed that the N-acetylornithine transaminase of P. stutzeri A1501 and the N-acetylornithine transaminase of the new microorganism had the base sequences of SEQ ID NO: 3 and SEQ ID NO: 4, respectively.

In the same manner, for comparative analysis of the base sequences for 4-aminobutyrate transaminase of P. stutzeri A1501 and the selected strain, gabT_F (5' primer: ATTTAACATATGCAACGCCGTGTCGCCGCCGTTCC; SEQ ID NO: 24) and gabT_R (3' primer: ATTTAAGAATTCTCAGGTCAGCTCGTCGAAACACT; SEQ ID NO: 25) were used to perform PCR. As a result, it was confirmed that P. stutzeri A1501 and the selected strain had the base sequences of SEQ ID NO: 5 and SEQ ID NO: 6, respectively.

For comparative analysis of the base sequences for N-acetylornithine transaminase of P. stutzeri A1501 and the selected strain, multiple sequence alignment was used. As a result, it was confirmed that 13 nucleic acids out of 1,221 nucleic acid sequences were different (nucleic acid homology: 98.9353%). In addition, in the same manner as the above, the results of comparative analysis of the nucleic acid sequences of 4-aminobutyrate transaminase of P. stutzeri A1501 and the selected strain confirmed that 21 nucleic acids out of 1,257 nucleic acid sequences were different (nucleic acid homology: 98.3294%).

In conclusion, it was confirmed that the selected P. stutzeri CJ-MKB strain had the highest homology with P. stutzeri A1501 among the known microorganism genomic sequences to date, and thus, it is a novel strain. Accordingly, the selected strain was deposited on Oct. 22, 2014 in the Korean Culture Center of Microorganisms, and was given accession number KCCM11587P.

Example 2: Identification of Deamination Reactivity of P. stutzeri CJ-MKB

P. stutzeri CJ-MKB was subjected to an evaluation of deamination reactivity of 5-aminovaleric acid and 6-aminocaproic acid. Since a transaminase reaction is a substitution reaction between an amine group and a ketone group, the substrates and the products were easily identified through a color reaction in which the reaction products that were subjected to material separation using thin layer chromatography (TLC) were able to be easily identified by color reaction of an amine group of ninhydrin. To confirm transaminase activity of P. stutzeri CJ-MKB, a whole cell reaction was performed. When P. stutzeri CJ-MKB was cultured and the optical density of the culture reached 0.7, the culture was sub-cultured on a new M9 medium. Here, 6-aminocaproic acid and 5-aminovaleric acid were fixed as a nitrogen source, and then cultured. Alpha-ketoglutarate and pyridoxal phosphate that are required for the medium were added to the culture, and to confirm the degree of deamination of 5-aminovaleric acid and 6-aminocaproic acid, TLC was performed thereon. Here, the reaction volume was 100 μl, and the production of glutamate and the degree of substrate degradation, which were dependent upon various concentrations of 5-aminovaleric acid, 6-aminocaproic acid, alpha-ketoglutarate, and pyridoxal phosphate and the presence and absence of each substrate, were confirmed on TLC. After the TLC development was completed, a material containing an amine group was developed with the 3% ninhydrin solution. According to the TLC results, it was confirmed that 5-aminovaleric acid and 6-aminocaproic acid was reduced, and glutamate was produced (see FIGS. 2A to 2F).

Figure 2A:
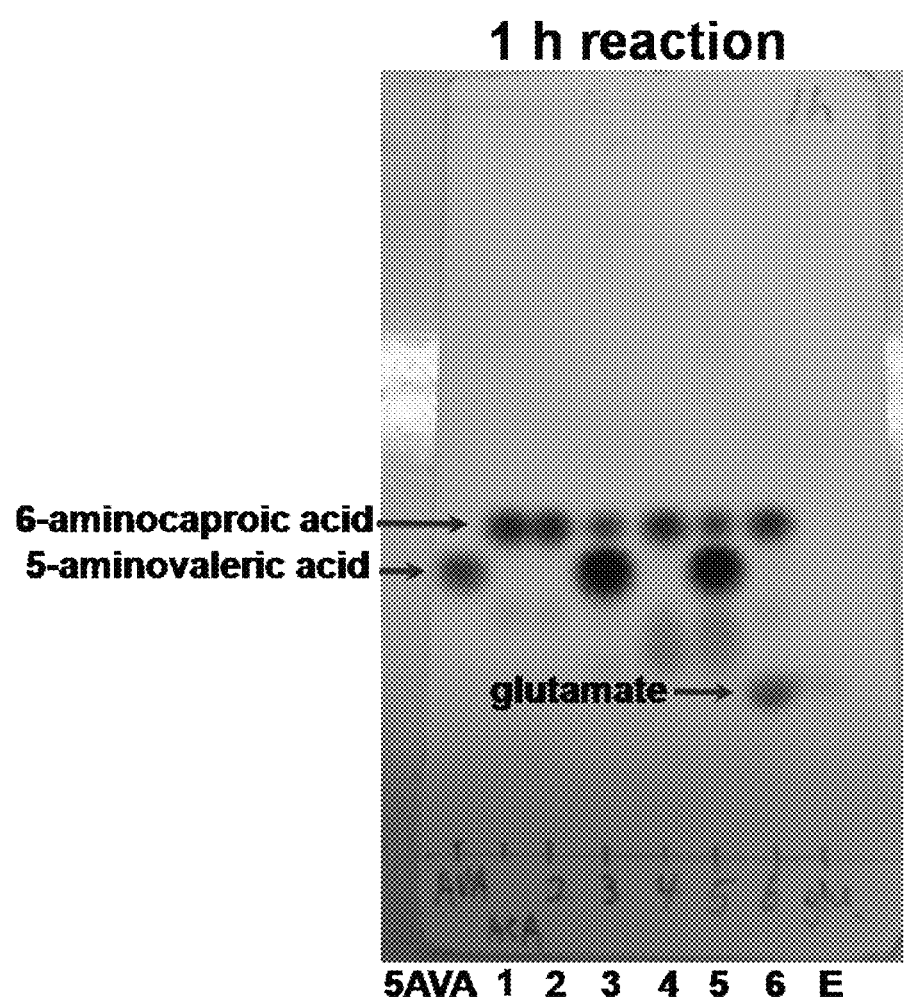
Figure 2B:
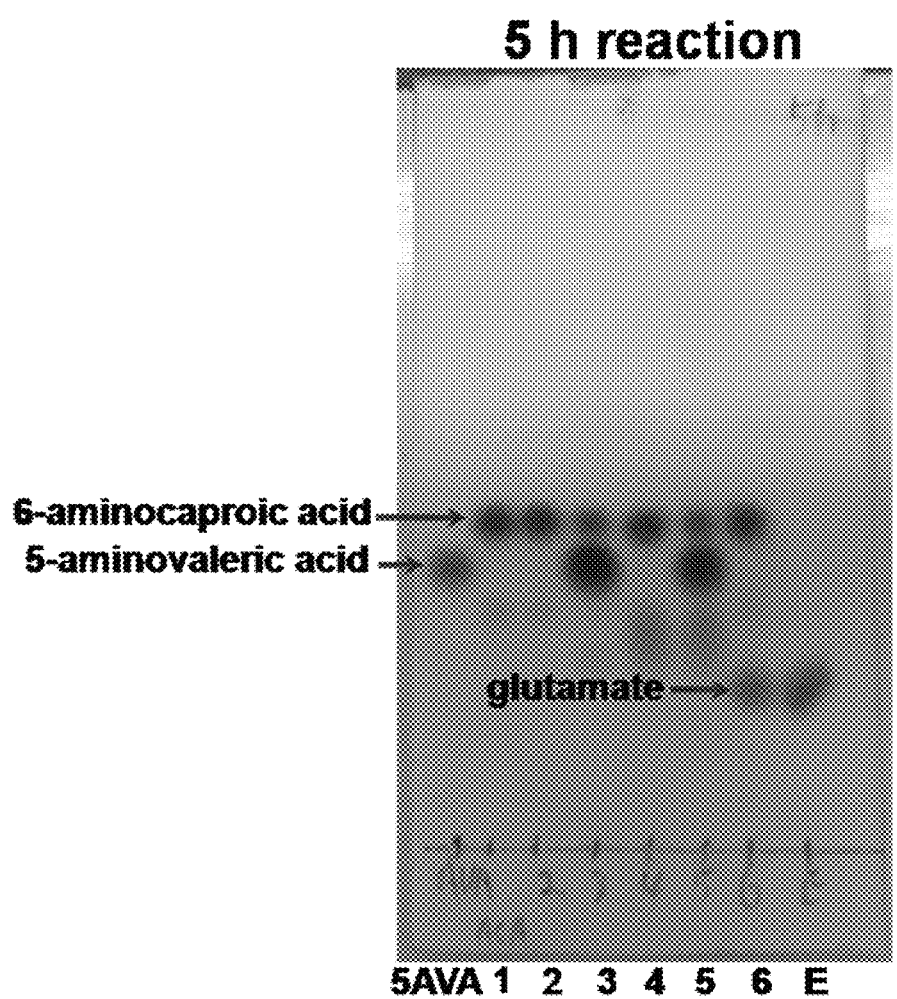
Figure 2C:
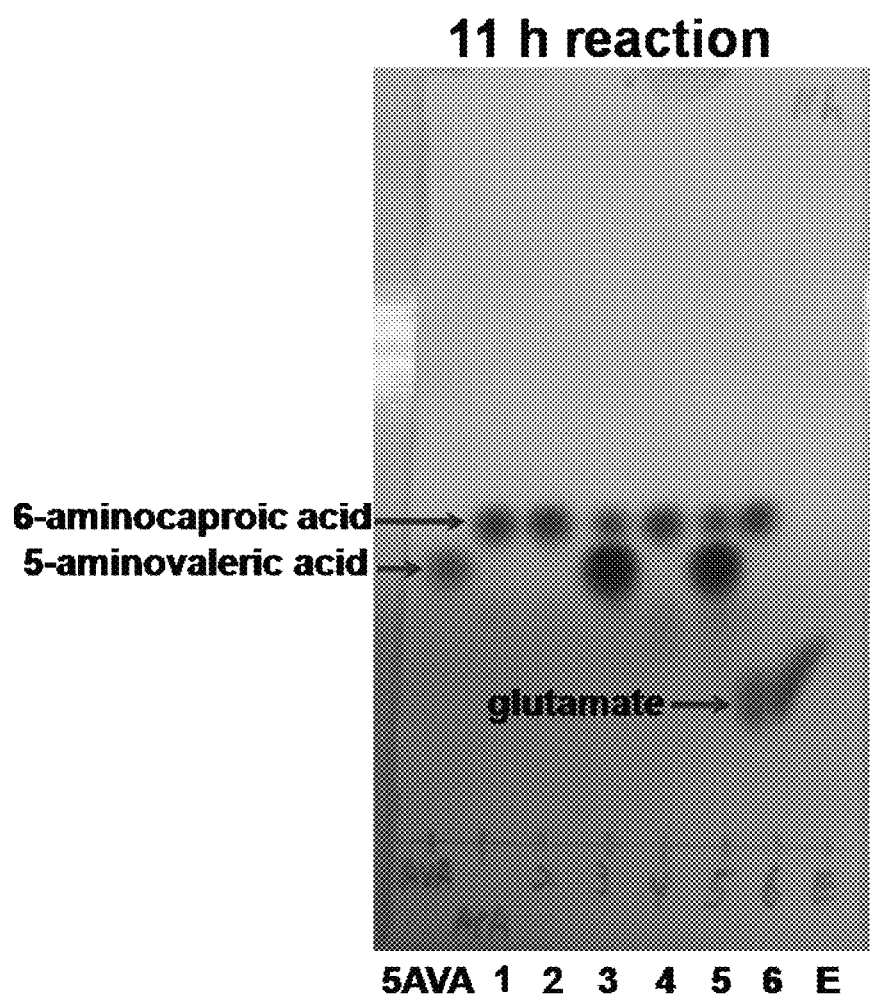
Figure 2D:
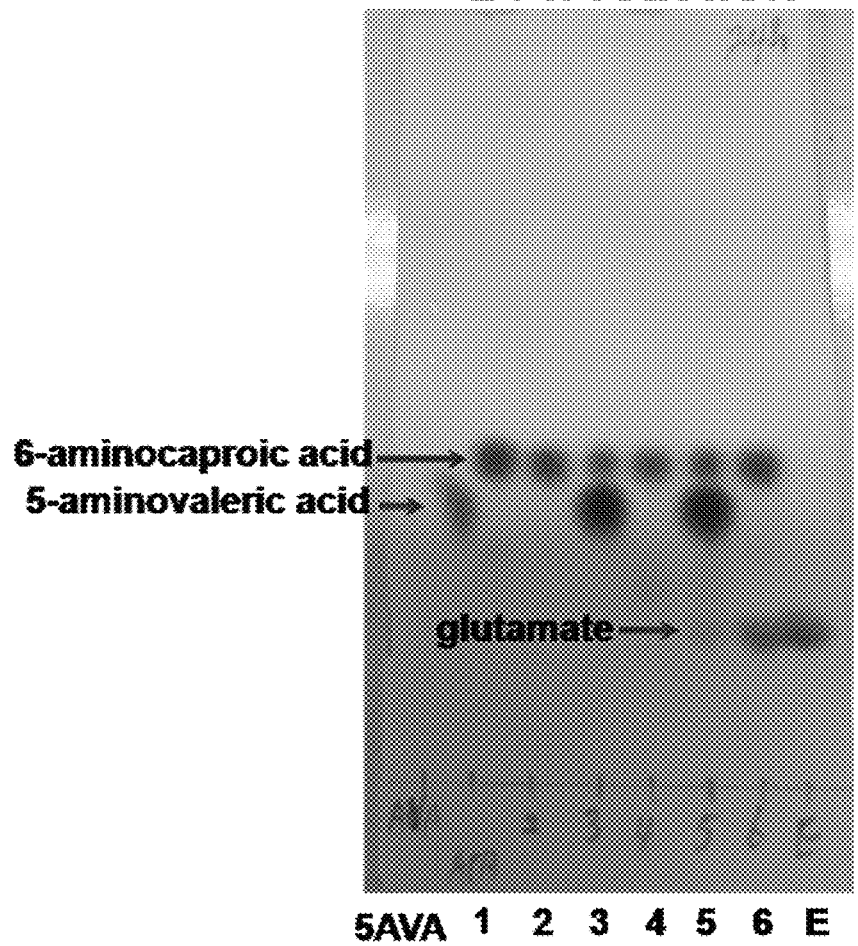
Figure 2E:
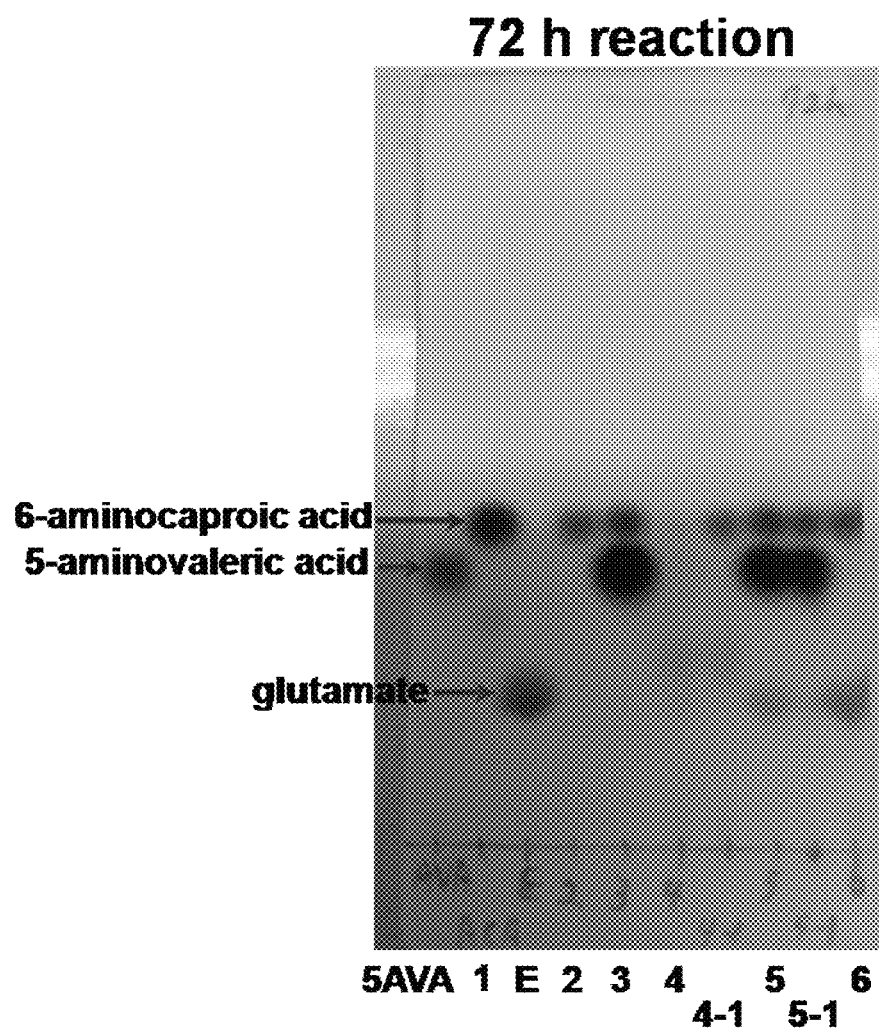
Figure 2F:
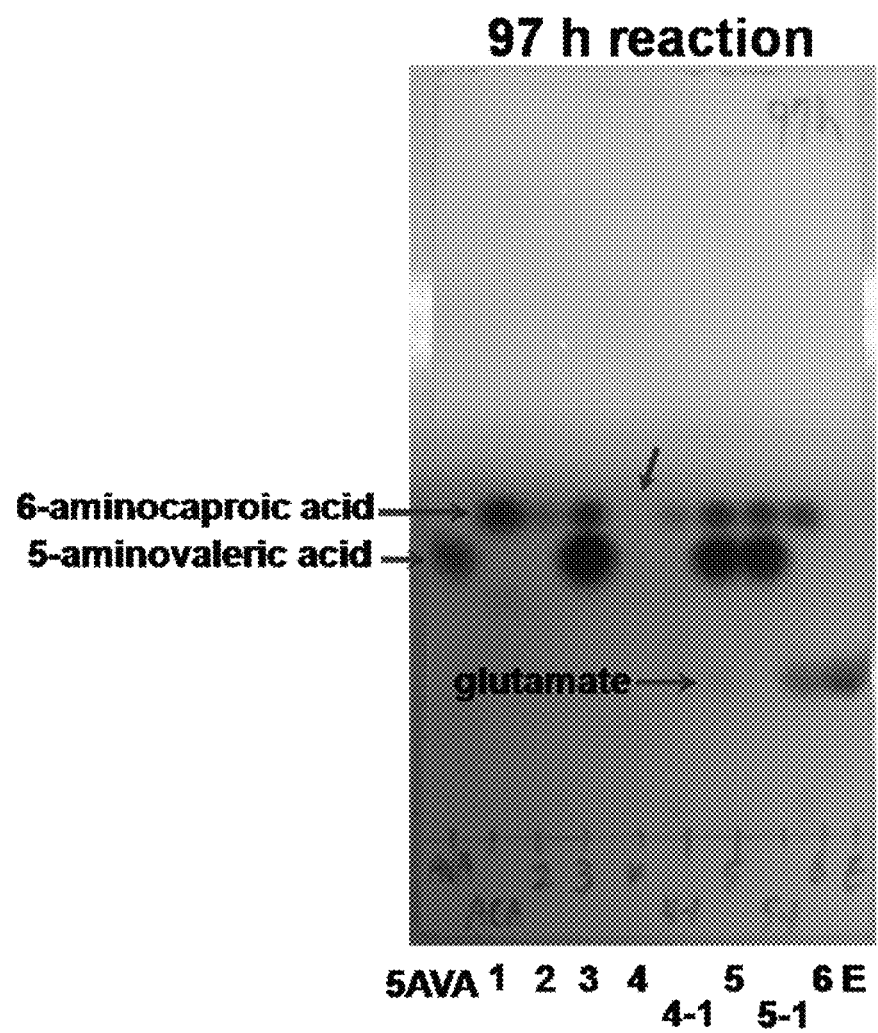

As shown in FIG. 2F (97 h reaction, lane 4), it was confirmed that the strain to which 20 mM of 6-aminocaproic acid, 10 mM of alpha-ketoglutarate, and 0.1 of mM pyridoxal phosphate were added reacted with all of the 6-aminocaproic acid before 97 hours. In comparison with a case where the transaminase reaction was satisfied, the reaction rate of the 6-aminocaproic acid was slow, but the decrease of 6-aminocaproic acid was observed on TLC even in the absence of pyridoxal phosphate (see FIG. 2F, 97 h reaction, lane 4-1). When 5-aminovaleric acid and 6-aminocaproic acid were present at the same time, the decrease of 6-aminocaproic acid was not confirmed (see FIG. 2F, 97 h reaction, lanes 5 and 5-1). In this regard, when P. stutzeri CJ-MKB was cultured under a minimal medium condition, it was evaluated that 6-aminocaproic acid and 5-aminovaleric acid compete to be a nitrogen source.

From this experimental result, it was confirmed that P. stutzeri CJ-MKB can use 6-aminocaproic acid as a single nitrogen source, and in the presence of alpha-ketoglutarate and pyridoxal phosphate, the deamination of 5-aminovaleric acid and 6-aminocaproic acid was accelerated (see FIGS. 2A to 2F). In FIGS. 2D and 2E (24 h reaction, lane 5; and 72 h reaction, lane 4), a small amount of glutamate was confirmed, but glutamate was not continuously accumulated.

Glutamate was produced in addition to the reaction of 6-aminocaproic acid, and most of the produced glutamate was used as an amine source, and thus it is evaluated that glutamate was rapidly converted without accumulating in cells.

Example 3: Induction of Overexpression of a New Polypeptide having Transaminase Activity of the Present Disclosure in an *E. coli* Strain, and Evaluation of Reactivity of the Polypeptide 1) Induction of Overexpression of a Polypeptide having Transaminase Activity and being Derived from *P. stutzeri* CJ-MKB strains in *E. coli* Strains To confirm the activity of an enzyme, which is presumed to be a transaminase and expected to be involved in the deamination reaction in the new *P. stutzeri* CJ-MKB strain that was selected and identified in Example 1, the following experiment was carried out. Through the sequence analysis, a base sequence of a gene (hereinafter, referred to as "argD") encoding the transaminase of the *P. stutzeri* CJ-MKB was confirmed (SEQ ID NO: 4).

For expression and purification, cloning was performed by adding a His-tag at the 5-terminal of the base sequence of argD for the expression. In detail, recombinant argD derived from the *P. stutzeri* CJ-MKB was introduced to *E. coli* Rosetta by using *E. coli* expression vector pETDuet1 (Merch Millipore, Darmstadt, Germany) to prepare a transformed strain. Then, the prepared transformed strain was added to a 3 mL LB broth medium to which 50 mg/ml of ampicillin was added, and the strain was cultured at a temperature of 37° C. for 12 hours. The cultured strain was cultured at a temperature of 37° C. in a 50 mL LB medium containing antibiotics. When the optical intensity thereof (at a wavelength of 600 nm) reached 0.8, expression was induced, and then, the strain was further cultured at a temperature of 18° C. for 48 hours. The cultured strain was washed and disrupted using a sonicator. Then, soluble proteins overexpressed after the disruption were identified by SDS-PAGE gel results (FIG. 3).

The transformed *E. coli* Rosetta was named '*E. coli* Rosetta 0004-0057', and deposited in the Korean Culture Center of Microorganisms (KCCM) on Oct. 22, 2014 under accession number of KCCM11588P.

2) Evaluation of Deamination Reactivity of Lysate of *E. coli* in which Polypeptides having Transaminase Activity of the Present Disclosure are Overexpressed The reactivity of each of the amino compounds (gamma-aminobutyric acid, 6-aminocaproic acid, and N-acetylornithine) was evaluated using the lysate of *E. coli* in which N-acetylornithine transaminase of Example 3-1 was overexpressed. 10 mM of each of the three amino compounds, 10 mM alpha-ketoglutarate, and 0.1 mM pyridoxal phosphate were added, and the activity of the overexpressed N-acetylornithine transaminase was evaluated. 50 μl of the lysate of *E. coli*, in which overexpression was induced, and substrates were added to 50 mM HEPES buffer (pH 8.0) to perform a reaction at a volume of 100 μl. After 30 minutes of the reaction ata temperature of 37° C., the degree of deamination of 6-aminocaproic acid was identified by TLC (FIG. 4).

The overexpressed N-acetylornithine transaminase was observed to be highly reactive with N-acetylornithine which is known to be an original substrate (Lane 8 of FIG. 4). In detail, it was observed that N-acetylornithine was significantly decreased while glutamate, which is a co-reactant of transaminase, was significantly increased. In addition, when a reaction was carried out with 6-aminocaproic acid as a substrate, the production of glutamate was observed with the unaided eye (Lane 5 of FIG. 4).

In addition, by increasing the concentration of 6-aminocaproic acid in the same manner as in the above-described reactivity evaluation, the amount of glutamate produced in the conversion reaction was analyzed by TLC (FIG. 5). As a result, as shown in the reaction (FIG. 5D), it was confirmed that, as the concentration of 6-aminocaproic acid was doubled (20 mM) or tripled (30 mM), glutamate production was increased. Accordingly, it was confirmed that the conversion of 6-aminocaproic acid by N-acetylornithine transaminase was a typical enzyme reaction in which the product increased as the substrate increased.

In conclusion, based on the above results, it was confirmed that, when the gene for a polypeptide having transaminase activity derived from *P. stutzeri* CJ-MKB was transformed and overexpressed in *E. coli*, the polypeptide of the present disclosure had deamination activity for 6-aminocaproic acid.

Example 4: Evaluation of Deamination Activity of N-acetylornithine Transaminase Derived from Various *Pseudomonas* Strains The deamination activity of the polypeptide for 6-aminocaproic acid was evaluated, wherein the polypeptide was derived from *P. stutzeri* CJ-MKB and had the transaminase activity of Example 3. In this regard, genes for N-acetylornithine transaminases derived from microorganisms of the genus *Pseudomonas*, such as *P. mendocina, P. putida, P. resinovorans, P. syringae*, and *P. thermotolerans*, that are considered to be capable of the same bioconversion reaction as the above, were expressed in *E. coli* for the evaluation of the reactivity thereof.

1) Comparison of Homology of N-acetylornithine Transaminases Derived from Various *Pseudomonas* Strains Five strains were selected from microorganisms of the genus *Pseudomonas*, and then, nucleotides provided by the National Center for Biotechnology Information (http://www.ncbi.nlm.nih.gov) and the genome program were used to identify genes and amino acid sequences for N-acetylornithine transaminases derived from *P. mendocina, P. putida, P. resinovorans, P. syringae*, and *P. thermotolerans*. Then, the homology with the amino acid sequence of the polypeptide derived from *P. stutzeri* CJ-MKB and having transaminase activity was compared (Table 2). Each of the enzymes derived from the microorganisms of the genus *Pseudomonas* showed at least about 75% homology with each other.

TABLE 2

Amino acid homology comparison results between N-acetylornithine transaminases derived from five microorganisms of the genus Pseudomonas and polypeptides derived from P. stutzeri CJ-MKB (unit: %)

| | P. resinovorans | P. thermotolerans | P. stutzeri CJ-MKB | P. mendocina | P. syringae | P. putida |
|---|---|---|---|---|---|---|
| P. resinovorans | | 86.1728 | 80.0493 | 78.0788 | 80.4938 | 83.4975 |
| P. thermotolerans | 86.1728 | | 78.0247 | 79.2593 | 78.2716 | 78.0247 |

TABLE 2-continued

Amino acid homology comparison results between N-acetylornithine transaminases derived from five microorganisms of the genus Pseudomonas and polypeptides derived from P. stutzeri CJ-MKB (unit: %)

|   | P. resinovorans | P. thermotolerans | P. stutzeri CJ-MKB | P. mendocina | P. syringae | P. putida |
|---|---|---|---|---|---|---|
| P. stutzeri CJ-MKB | 80.0493 | 78.0247 |  | 76.3547 | 75.3086 | 78.0788 |
| P. mendocina | 78.0788 | 79.2593 | 76.3547 |  | 80.9877 | 80.2956 |
| P. syringae | 80.4938 | 78.2716 | 75.3086 | 80.9877 |  | 79.0123 |
| P. putida | 83.4975 | 78.0247 | 78.0788 | 80.2956 | 79.0123 |  |

2) Separation and Purification of N-acetylornithine Transaminases Derived from Five *Pseudomonas* Strains and Polypeptide of the Present Disclosure The genes for N-acetylornithine transaminases of five *Pseudomonas* strains and the gene for the polypeptide having transaminase activity derived from *P. stutzeri* CJ-MKB of the present disclosure in Example 4-1 were obtained, and expressed in *E. coli* in the same manner as in Example 3-1. Then, proteins purified using the His-tag column were obtained. As a result of comparing the obtained proteins on SDS-PAGE gel, it was confirmed that the proteins were purified in a normal manner (FIG. 6).

3) Evaluation of Deamination Activity of N-acetylornithine Transaminases Derived from Five *Pseudomonas* Strains and the Polypeptide of the Present Disclosure for 6-aminocaproic Acid The reactivities of the proteins purified in Example 4-2 for 6-aminocaproic acid were verified (Lanes 3, 5, 7, 9, 11, and 13 of FIG. 6). In detail, to a reaction solution containing 20 mM 6-aminocaproic acid, 10 mM alpha-keto glutamate, and 0.1 mM pyridoxal phosphate, each purified N-acetylornithine transaminase was added at a concentration of 0.5 mg/ml of the total reaction solution. 50 mM HEPES (pH 8.0) was then added to the mixed solution, and a reaction was performed at a volume of 100 µl. After 1 hour of reaction at a temperature of 37° C., 10 µl of the reaction-completed sample was diluted with 990 µl of ethanol to remove enzyme activity. Afterwards, under conditions of a speed of 14,000 rpm, a temperature of 4° C., and a reaction time of 10 minutes, centrifugation was performed, and 10 µl of the supernatant was diluted with 990 µl of sterilized distilled water. Then, liquid chromatography-mass spectrometer LC-MASS was used to analyze the degree of reduction of 6-aminocaproic acid.

As a result, it was confirmed that the N-acetylornithine transaminase derived from *P. syringae* showed 56.69% conversion of 6-aminocaproic acid, whereas the polypeptide derived from *P. stutzeri* CJ-MKB showed 45.52% conversion of 6-aminocaproic acid in a similar manner to the other compared strains.

The same sample was used to compare the degree of aldehyde formation by using the relative activity values using Schiff's reagent (FIG. 8). In a reaction of 20 mM 6-aminocaproic acid, 10 µl of the reactant was diluted with 180 µl of 50 mM HEPES buffer (pH 8.0), and 10 µl of the Schiff's reagent was added thereto for a reaction at room temperature for 30 minutes. Here, an enzyme sample to which a substrate was not added and a substrate sample to which only a substrate was added were used as control samples. Relative enzymatic activities were compared using a 96-well plate reader based on absorbance values at a wavelength of 490 nm (FIG. 8).

The aldehyde production in the reaction sample of the N-acetylornithine transaminase derived from *P. thermotolerans* was measured as higher than the LC-Mass results, but the overall reaction degree was confirmed in the same order. In addition, it was confirmed that the LC-Mass results and the Schiff's reagent results had a correlation.

4) Evaluation of Deamination Activities of N-acetylornithine Transaminases Derived from Genus *Pseudomonas* Strains and the Polypeptide of the Present Disclosure for N-acetylornithine, gamma-aminobutyric Acid, and 5-aminovaleric Acid Substrates With respect to various substrates, the reactivities of the N-acetylornithine transaminases, which were derived from five microorganisms of the genus *Pseudomonas* and of which reactivities were identified in Example 4-3, and reactivities of the polypeptide of the present disclosure, were evaluated. Along with 10 mM alpha-keto glutamate and 0.1 mM pyridoxal phosphate, N-acetylornithine, gamma-aminobutyric acid, or 5-aminovaleric acid was added at a concentration of 10 mM of the total reaction solution, and N-acetylornithine transaminase was added at a concentration of 0.5 mg/ml of the total reaction solution, for a reaction at a temperature of 37° C. for 1 hour. 10 µl out of 100 µl of the reactant was diluted with 180 µl of 50 mM HEPES buffer (pH 8.0), and 10 µl of Schiff's reagent was used for a reaction for 30 minutes. Then, a 96-well plate reader was used to compare relative enzymatic activities.

The deamination reaction of N-acetylornithine, which is known as the original substrate of N-acetylornithine transaminase, showed the highest activity when derived from *P. mendocina* (FIG. 9).

Regarding gamma-aminobutyric acid, the highest reactivity was shown for the N-acetylornithine transaminase derived from *P. resinovorans* (FIG. 10).

Regarding 5-aminovaleric acid, the highest reactivity was shown for the polypeptide derived from *P. stutzeri* CJ-MKB (FIG. 11).

Example 5: Evaluation of Reverse-Reaction Activity of Polypeptide having Transaminase Activity Derived from *P. stutzeri* CJ-MKB According to Example 4, it was confirmed that the N-acetylornithine transaminases derived from various *Pseudomonas* strains and the polypeptide of the present disclosure were converted to adipate semialdehyde and the like by deamination of an amine compound, such as 6-aminocaproic acid. In Example 5, as a reverse reaction of the reaction of Example 4, for confirming the conversion reactivity from adipate semialdehyde to 6-aminocaproic acid, excess glutamate was treated in the presence of adipate semialdehyde produced by N-acetylornithine transaminase to thereby confirm whether adipate semialdehyde was produced to 6-aminocaproic acid.

First, 5 mM 6-aminocaproic acid, 5 mM alpha-ketoglutarate, and 0.1 mM pyridoxal phosphate were prepared with 50 mM HEPES buffer (pH 8.0) at a volume of 100 μl, and N-acetylornithine transaminases derived from five Pseudomonas strains and the polypeptide of the present disclosure were added thereto at a concentration of 0.5 mg/ml of the total reaction solution, thereby performing a reaction at a temperature of 37° C. for 1 hour. After the completion of the reaction, the reaction sample was treated at a temperature of 100° C. for at least 5 minutes to thereby remove the enzyme activity. The heat-treated sample was centrifuged at a speed of 14,000 rpm for 10 minutes at a temperature 4° C., and then, 10 μl of the supernatant was diluted with 180 μl of 50 mM HEPES buffer (pH 8.0) (forward reaction, alpha-ketoglutarate (α-KG) reaction), In addition, to induce a reverse reaction of the reaction above, a sample having a volume of 200 μl was prepared and treated under the same conditions as above. After performing centrifugation thereon, 20 mM glutamate and 0.5 mg/ml of enzyme were added to 97 μl of the supernatant. Then, at a volume of 100 μl, the reaction sample was reacted at a temperature of 37° C. for 1 hour, followed by treatment at a temperature of 100° C. for 5 minutes. Afterwards, centrifugation was performed thereon at a speed of 14,000 rpm for 10 minutes at a temperature 4° C., and then, 10 μl of the supernatant was diluted with 180 μl of 50 mM HEPES buffer (pH 8.0) (reverse reaction, glutamate reaction).

The obtained sample was reacted with 10 μl of Schiff's reagent for 30 minutes, and a 96-well plate reader was used to compare the relative enzymatic activities. As a result, when comparing the values obtained using a 96-well plate reader after the reaction of the Schiff's reagent, it was confirmed that the N-acetylornithine transaminases derived from 5 Pseudomonas strains and the polypeptide of the present disclosure converted adipate semialdehyde to 6-aminocaproic acid (FIG. 12).

The invention claimed is:

1. A method of deaminating an amino compound, the method comprising:
   adding a polypeptide having transaminase activity for an amino compound to a solution containing the amino compound, wherein the polypeptide has the amino acid sequence of SEQ ID NO: 7, 9, 11, 13, 15, or 17, and wherein the amino compound is at least one selected from the group consisting of gamma-aminobutyric acid, 5-aminovaleric acid, and 6-aminocaproic acid.

2. The method of claim 1, wherein the solution further contains pyridoxal phosphate, in addition to at least one selected from the group consisting of pyruvate, oxaloacetate, and alpha-ketoglutarate.

* * * * *

SEQUENCE LISTING

<160> NUMBER OF SEQ ID NOS: 25

<210> SEQ ID NO 1
<211> LENGTH: 1384
<212> TYPE: DNA
<213> ORGANISM: Pseudomonas stutzeri CJ-MKB

<400> SEQUENCE: 1

```
tgcagtcgag cggatgaatg gagcttgctc catgattcag cggcggacgg gtgagtaatg      60
cctaggaatc tgcctggtag tgggggacaa cgtttcgaaa ggaacgctaa taccgcatac     120
gtcctacggg agaaagtggg ggatcttcgg acctcacgct atcagatgag cctaggtcgg     180
attagctagt tggtgaggta aaggctcacc aaggcgacga tccgtaactg gtctgagagg     240
atgatcagtc acactggaac tgagacacgg tccagactcc tacgggaggc agcagtgggg     300
aatattggac aatgggcgaa agcctgatcc agccatgccg cgtgtgtgaa gaaggtcttc     360
ggattgtaaa gcactttaag ttgggaggaa gggcagtaag ttaataccct gctgttttga     420
cgttaccaac agaataagca ccggctaact tcgtgccagc agccgcggta atacgaaggg     480
tgcaagcgtt aatcggaatt actgggcgta aagcgcgcgt aggtggttcg ttaagttgga     540
tgtgaaagcc ccgggctcaa cctgggaact gcatccaaaa ctggcgagct agagtatggc     600
agagggtggt ggaatttcct gtgtagcggt gaaatgcgta gatataggaa ggaacaccag     660
tggcgaaggc gaccacctgg gctaatactg acactgaggt gcgaaagcgt ggggagcaaa     720
caggattaga taccctggta gtccacgccg taaacgatgt cgactagccg ttgggatcct     780
tgagatctta gtggcgcagc taacgcatta agtcgaccgc ctggggagta cggccgcaag     840
gttaaaactc aaatgaattg acggggggcc gcacaagcgg tggagcatgt ggtttaattc     900
gaagcaacgc gaagaacctt accaggcctt gacatgcaga gaacttccca gagatggatt     960
ggtgccttcg ggaactctga cacaggtgct gcatggctgt cgtcagctcg tgtcgtgaga    1020
tgttgggtta agtcccgtaa cgagcgcaac ccttgtcctt agttaccagc acgttaaggt    1080
gggcactcta aggagactgc cggtgacaaa ccggaggaag gtggggatga cgtcaagtca    1140
tcatggccct tacggcctgg gctacacacg tgctacaatg gtcggtacaa agggttgcca    1200
agccgcgagg tggagctaat cccataaaac cgatcgtagt ccggatcgca gtctgcaact    1260
cgactgcgtg aagtcggaat cgctagtaat cgtgaatcag aatgtcacgg tgaatacgtt    1320
```

```
cccgggccett gtacacaccg cccgtcacac catgggagtg ggttgctcca gaagtagcta    1380
gtct                                                                 1384

<210> SEQ ID NO 2
<211> LENGTH: 714
<212> TYPE: DNA
<213> ORGANISM: Pseudomonas stutzeri CJ-MKB

<400> SEQUENCE: 2
agcccttcct cgaacagggt gttgagcagg ccgaacaaca gcgcggcgtc ctgtccgggg      60
cgcacgaaca gatgttgatc ggcgatggcg gcggtctcgc tgcgccgcgg gtcgaccacc     120
accagtttgc cgccgcgggc gcggatcgcc ttcagccgct tctccacatc gggcacggtc     180
atgatgctac cgttggaggc caaaggggttg ccgccgagaa tcagcatgaa atcggtgtga     240
tcgatgtccg gcaccggcag cagcagacca tggccgtaca tcaggtggct ggtcaggtgg     300
tgcggcagct ggtcgaccga cgtggccgag aagcggttgc gcgtcttcag cagaccgagg     360
aagtaattgc tgtgggtcgt cagcccgtag ttatgcacac tcgggttgcc ttggtagatc     420
gccacggcat tactaccgtg gcgctcgcgg atctcagcca ggcgctcggc gaccagttcg     480
taggcctcct cccagctgat ggcctgccac tcatcgccgc agcggcgcat cggtggcgc      540 aggcgatcgg ggtcgttctg gatgtcctgc agcgccactg ccttcggaca gatatggccg     600
cggctgaagc tgtcgagggg atcgcccttg atcgaaagga tgcgctcgcc ttcggtctgg     660
atggtcaggc cgcagatggc ttcgcacagg tgacaggcac ggtgatggac gctg           714

<210> SEQ ID NO 3
<211> LENGTH: 1221
<212> TYPE: DNA
<213> ORGANISM: Pseudomonas stutzeri A1501

<400> SEQUENCE: 3
atgtccgccc cgcacacccc ggtagaacgc gccgatttcg accaggtcat tgttcccact      60
ttcgcccccg ccgccttcgt gccggtgcgt ggtctgggct cgcgagtatg ggatcagagc     120
ggtcgagaac tggtggactt cgctggcggc atcgcggtta acgccctggg ccatgcccat     180
ccggccatga tcgcggcact gacggagcag gctggcaagc tctggcacat ctccaacatc     240
tataccaacg agccggcgct cgcgcctggcc aaaaagctgg tggcggcgac cttcgccgac     300
cgcgccttct tctgcaattc cggcgcagag gccaacgagt cggcgttcaa actggcccgt     360
cgctacgccc atgatgtgta tggcccgcag aaattcgaga tcatctcggc gctcaacagc     420
ttccacggcc gcaccctgtt caccgtcacg gtgggcgggc agtcgaagta ctccgatggc     480 tcgggccga agatcgaagg catcactcac gtgccttaca cgacctcga agcgctgaag     540 gcggcgatct ccgacaagac ctgtgccgtg gtgctcgaac cgatccaggg cgagagcggc     600
atcctgccgg gcgagcaggc gtacctggaa ggtgcacgcc agctgtgcaa cgagcacaac     660
gcgctgctga tcttcgatga ggtgcagacc ggtctaggcc gtaccggtga gctgttcgcc     720
tacatgcact atggcgtcac gccggacatt ctgaccaacg ccaagagcct gggtggcggc     780
ttcccgatcg gtgcgatgct gaccaccaac gagatcgccg cccatttcag cgtcggtacc     840
cacggcacca cgtacggcgg caatccgctg gcctgcgcgg tggccgagac ggtgctggat     900
atcgtcaaca cccggaggt gctggagggc gtcaaggccc gccacgagcg cttcaaggcc     960
cggctgttgc agatcggtga gcgctacggc gtgttcagcc aggtccgcgg ccgtggcctg    1020
ttgatcggct gcgtgctctc ggatgcctgg aaaggcaagg ccggtgcatt ctgggccgcg    1080
```

```
gcggagaagg aggcgctgat ggtgctgcag gcagggccgg acgtggttcg cctggcgccg    1140
agtctgatca tcgacgaagc tgacatagac gaggggctgg atcgtttcga gcgcgccatc    1200
gcgacgctga cccaggcctg a                                              1221
```

<210> SEQ ID NO 4
<211> LENGTH: 1221
<212> TYPE: DNA
<213> ORGANISM: Pseudomonas stutzeri CJ-MKB

<400> SEQUENCE: 4

```
gtgtccgccc cgcacacccc ggtagaacgc gccgatttcg accaggtcat tgttcccact     60
ttcgcccccg ccgccttcgt gccggtgcgt ggtctgggct cgcgagtatg ggatcagagc    120
ggtcgagaac tggtggactt cgctggcggc atcgcggtca acgccctggg ccatgcccat    180
ccggccatga tcgcggcact gacggagcag gctggcaagc tctggcacat ctccaacatc    240
tataccaacg agccggcgct gcgcctggcc aagaagctgg tggcggcgac cttcgccgac    300
cgcgccttct tctgcaattc cggtgcagag gccaacgagg cggcgttcaa actgcccgt     360 cgctacgccc atgatgtgta cggcccgcag aagttcgaga tcatctcggc gctcaacagc    420
ttccacggcc gcaccctgtt caccgtcacg gtgggcgggg agtcgaagta ctccgatggc    480
ttcgggccga agatcgaagg cattactcac gtgccttaca cgacctcga agcgctgaag    540 gcggcgatct ccgacaagac ctgtgccgtg gtgctcgaac cgatccaggg cgagagcggc    600
atcctgccgg gcgaacaggc gtacctggaa ggcgcacgcc agctgtgcaa cgagcacaac    660
gcgctgctga tcttcgatga ggtgcagacc ggtctgggcc gtaccggtga gctgttcgcc    720
tacatgcact atggcgtcac gccggacatt ctgaccaacg ccaagagcct tggtggcggc    780
ttcccgatcg gtgcgatgct gaccaccaac gagatcgccg cccatttcag cgtcggtacc    840
cacggcacca cgtacggcgg caatccgctg gcctgcgcgg tggccgagac ggtgctggat    900
atcgtcaaca ccccggaggt gctggagggc gtcaaggccg ccacgagcg cttcaaggcc     960 aggctgttgc agatcggtga gcgctacggc gtgttcagcc aggtccgcgg ccgcggcctg   1020
ttgatcggct gcgtgctctc ggatgcctgg aaaggcaagg ccggtgcatt ctgggccgcg   1080
gcggagaagg aggcgctgat ggtgctgcag gcagggccgg acgtggttcg cctggcgccg   1140
agtctgatca tcgacgaagc tgacatagac gaggggctgg atcgtttcga gcgcgccatc   1200
gcgacgctga cccaggcctg a                                             1221
```

<210> SEQ ID NO 5
<211> LENGTH: 1257
<212> TYPE: DNA
<213> ORGANISM: Pseudomonas stutzeri A1501

<400> SEQUENCE: 5

```
atgcaacgcc gtgtcgccgc cgttccccgt ggcgtcggcc agatccaccc gatctttgcc     60
gaccacgcga agaacagcag cgtggtggat gtggagggcc gcgagttcat cgatttcgcc    120
ggcggcatcg ccgtgctgaa taccggccac ctgcacccga agatcgtcaa ggcggtggaa    180
gaccagctgc acaagctcac ccacacctgc ttccaggtgc tggcctacga gccgtacgtc    240
gagctgtgcg agaagatcaa cgccgggtg ccgggtgatt cgccaagaa gactctgctg      300 gtcaccaccg gctccgaggc cgtggagaac gcggtgaaga tcgcccgcgc cgccaccggc    360
cgtgccggcg tgattgcctt caccggcgcc tatcacggcc gcaccatgat gaccctcggc    420
```

```
ctgaccggca aggtcgcccc gtactccgcc ggcatgggcc tgatgccggg cgggatcttc      480
cgtgcgcagt atccctgcgc gatccatggt gtcagcgtcg atgactcgat cgcgagcatc      540
gagcgcatct tcaagaacga tgccgagccg cgcgacatcg ccgcgatcat cgtcgaaccg      600
gtgcagggcg agggcggctt caatgtcgcg ccgaaggatt tcatggcccg cctgcgcgcg      660
ctctgcgacg agcacggcat cctgctgatc gccgacgagg tgcagaccgg cgccgggcgc      720
accggcacct tcttcgccat ggagcagatg ggcgtggtcg ccgacctgac caccttcgcc      780
aagtcggtcg gcggcggctt cccgatcgcc ggcgtgtgcg gcaaggccga gatcatggat      840
gccatcgcac ccggcgggct gggcggcacc tatgccggca accgttgtc ctgcgcggcg       900 gcgctggcgg tcatggaaat cttcgaggag gagcatctgc tcgaccgctg caaggccgtg      960
gcggagaagc tcaccaccgg cctcaaggcg atccaggcca agcacaagga gatcggcgag     1020
gtgcgcggcc tcgcgcgat gatcgccatc gagctgttcg aggatggcga cctggcgcga      1080
ccggccgcgg cgctcacgtc gcagatcgtc gcccgggcgc gggagaaggg attgatcctg     1140
ctgtcctgcg gtacctacta caacgtgctg cgcgtgctgg tgccgctgac cgtcgaggac     1200
gagctgctcg agcgcggcct ggccatcctc ggcgagtgtt tcgacgagct gacctga       1257
```

<210> SEQ ID NO 6
<211> LENGTH: 1257
<212> TYPE: DNA
<213> ORGANISM: Pseudomonas stutzeri CJ-MKB

<400> SEQUENCE: 6

```
atgcaacgcc gtgtctccgc cgttccccgt ggcgtcggcc agatccaccc gatctttgcc       60
gaccacgcga agaacagcag cgtggtggat gtggaggggc gccagttcat cgatttcgcc      120
ggcggcaacg ccgtgctgaa taccggccac ctgcacccga gatcgtcaa ggcggtggaa       180 gaccagctgc acaagctcac ccacacctgc ttccaggtgc tggcctacga gccgtacgtc      240
gagctgtgcg agaagatcaa cgcgcgggtg ccgggtgatt cgccaagaa gactctgctg       300 gtcaccaccg gctccgaggc cgtggagaac gcggtgaaga tcgcccgcgc cgccaccggc      360
cgtgccggcg tcattgcctt caccggcgcc tatcacggcc gcaccatgat gaccctcggc      420
ctgaccggca aggtcgcccc gtactccgcc ggcatgggcc tgatgccggg cgggatcttc      480
cgtgcgcagt accctgcgc gatccatggt gtcagcgtcg atgactcgat cgcgagcatc       540
gagcgcatct tcaagaacga cgccgagccg cgcgacatcg ccgcgatcat cgtcgaaccg      600
gtgcagggcg agggcggctt caatgtcgcg ccgaaggatt tcatggcccg cctgcgcgcg      660
ctctgcgacg agcacggcat cctgctgatc gccgacgagg tgcagaccgg cgccggacgc      720
accggcacct tcttcgccat ggagcagatg ggcgtggtcg ccgatctgac caccttcgcc      780
aagtcggtcg gcggcggctt cccgatcgcc ggcgtgtgcg gcaaggccga gatcatggat      840
gccatcgcgc ccggcgggct gggcggcacc tatgccggca accgctgtc ttgcgcggcg       900 gcgctggcgg tcatggaaat cttcgaggag gagcatctgc tcgaccgctg caaggcggtg      960
gcggagaagc tcaccaccgg cctcaaggcg atccaggcca agcataagga gatcggcgag     1020
gtgcgcggcc tcgcgcgat gatcgccatc gagctgttcg aggatggcga cctggcgcga      1080
ccggccgcgg cgctgacgtc gcagatcgtc gcccgggcgc gggacaaggg gctgatcctg     1140
ttgtcctgcg gtacctacta caacgtgctg cgcgtgctgg tgccgctgac cgtcgaggac     1200
gagctgtacg agcgcggcct ggccatcctc ggcgagtgtt tcgacgagct gacctga       1257
```

```
<210> SEQ ID NO 7
<211> LENGTH: 406
<212> TYPE: PRT
<213> ORGANISM: Pseudomonas stutzeri CJ-MKB

<400> SEQUENCE: 7

Met Ser Ala Pro His Thr Pro Val Glu Arg Ala Asp Phe Asp Gln Val
1               5                   10                  15

Ile Val Pro Thr Phe Ala Pro Ala Phe Val Pro Val Arg Gly Leu
            20                  25                  30

Gly Ser Arg Val Trp Asp Gln Ser Gly Arg Glu Leu Val Asp Phe Ala
        35                  40                  45

Gly Gly Ile Ala Val Asn Ala Leu Gly His Ala His Pro Ala Met Ile
    50                  55                  60

Ala Ala Leu Thr Glu Gln Ala Gly Lys Leu Trp His Ile Ser Asn Ile
65                  70                  75                  80

Tyr Thr Asn Glu Pro Ala Leu Arg Leu Ala Lys Lys Leu Val Ala Ala
                85                  90                  95

Thr Phe Ala Asp Arg Ala Phe Phe Cys Asn Ser Gly Ala Glu Ala Asn
            100                 105                 110

Glu Ala Ala Phe Lys Leu Ala Arg Arg Tyr Ala His Asp Val Tyr Gly
        115                 120                 125

Pro Gln Lys Phe Glu Ile Ile Ser Ala Leu Asn Ser Phe His Gly Arg
    130                 135                 140

Thr Leu Phe Thr Val Thr Val Gly Gly Gln Ser Lys Tyr Ser Asp Gly
145                 150                 155                 160

Phe Gly Pro Lys Ile Glu Gly Ile Thr His Val Pro Tyr Asn Asp Leu
                165                 170                 175

Glu Ala Leu Lys Ala Ala Ile Ser Asp Lys Thr Cys Ala Val Val Leu
            180                 185                 190

Glu Pro Ile Gln Gly Glu Ser Gly Ile Leu Pro Gly Glu Gln Ala Tyr
        195                 200                 205

Leu Glu Gly Ala Arg Gln Leu Cys Asn Glu His Asn Ala Leu Leu Ile
    210                 215                 220

Phe Asp Glu Val Gln Thr Gly Leu Gly Arg Thr Gly Glu Leu Phe Ala
225                 230                 235                 240

Tyr Met His Tyr Gly Val Thr Pro Asp Ile Leu Thr Asn Ala Lys Ser
                245                 250                 255

Leu Gly Gly Gly Phe Pro Ile Gly Ala Met Leu Thr Thr Asn Glu Ile
            260                 265                 270

Ala Ala His Phe Ser Val Gly Thr His Gly Thr Thr Tyr Gly Gly Asn
        275                 280                 285

Pro Leu Ala Cys Ala Val Ala Glu Thr Val Leu Asp Ile Val Asn Thr
    290                 295                 300

Pro Glu Val Leu Glu Gly Val Lys Ala Arg His Glu Arg Phe Lys Ala
305                 310                 315                 320

Arg Leu Leu Gln Ile Gly Glu Arg Tyr Gly Val Phe Ser Gln Val Arg
                325                 330                 335

Gly Arg Gly Leu Leu Ile Gly Cys Val Leu Ser Asp Ala Trp Lys Gly
            340                 345                 350

Lys Ala Gly Ala Phe Trp Ala Ala Ala Glu Lys Glu Ala Leu Met Val
        355                 360                 365

Leu Gln Ala Gly Pro Asp Val Val Arg Leu Ala Pro Ser Leu Ile Ile
    370                 375                 380
```

Asp Glu Ala Asp Ile Asp Glu Gly Leu Asp Arg Phe Glu Arg Ala Ile
385                 390                 395                 400

Ala Thr Leu Thr Gln Ala
            405

<210> SEQ ID NO 8
<211> LENGTH: 1221
<212> TYPE: DNA
<213> ORGANISM: Pseudomonas mendocina

<400> SEQUENCE: 8

```
atgtctgttc agcacgatgc ggtgcaacgc gccgatttcg accagtacat ggtccccaac     60
tacgccctg ccgccttcgt acccgtgcgt ggcctcggtt cgcgagtctg ggatcagagt    120
ggtcgagagc tgatcgactt cgccggcggc atcgccgtca acgtgcttgg ccactgccat    180
ccggcgctgg tcgcggcgct gaccgagcag gccaacaccc tctggcacat ctccaacgtg    240
ttcaccaacg agccgaccct cgcctgggc aagaagctgg tcgatgcgac cttcgccgag    300
cgcgtgttct tctgcaactc tggcgccgag gccaacgagg ccgcgttcaa gctggcccgt    360
cgtgttgcgc atgaccgttt cggcccggaa aagcacgaga tcattgccgc gctcaacagc    420
ttccacggcc gtaccctgtt caccgtcagc gtcggcggcc agccgaagta ctccgacggc    480
ttcggtccga agatccaggg catcacccac gtgccctaca cgatctggga ggcgctgaag    540
gcggccattt ccgacaagac ctgcgcagtg gtactcgagc cgatccaggg cgagggcggc    600
gtgctgccgg ccgagaaagc ctacctggaa ggcgcccgtg agctgtgcaa cgcgcacaac    660
gcgctgctgg tattcgacga ggtgcagagc ggcatgggcc gcagcggcga actgttcgcc    720
tacatgcact atggtgtggt gccggacatt ctctccagcg ccaagagcct gggggtggc    780
ttccccatcg ccgccatgct caccaccacc gacctggcca gcactttac ccccggtacc    840
cacggcacca cctatggtgg caacccgctg gcctgcgcag tgggcgaggc ggtgctggac    900
atcgtcaata cccgcgagac cctggatggc gtgaaggtca gcaccagca gttcaagcaa    960
cgcctggagg cgctcggcaa gcagttcggt ctgttcgagc aggtgcgcgg catgggcctg   1020
ctgctcggtt gcgtgctcaa cgaggcgtgg aagggcaagg ccaagcaggt gctggacgcc   1080
gcttccgcgg aagggctgat gattctgcag gccggtccgg acgtggtgcg tttcgccccg   1140
agcctggtgg tggaagagcg cgatatcgaa gaaggcctgg cccgtttcga gcgtgcgctg   1200
agcaagctgg ccaacgcctg a                                            1221
```

<210> SEQ ID NO 9
<211> LENGTH: 406
<212> TYPE: PRT
<213> ORGANISM: Pseudomonas mendocina

<400> SEQUENCE: 9

Met Ser Val Gln His Asp Ala Val Gln Arg Ala Asp Phe Asp Gln Tyr
1               5                   10                  15

Met Val Pro Asn Tyr Ala Pro Ala Ala Phe Val Pro Val Arg Gly Leu
            20                  25                  30

Gly Ser Arg Val Trp Asp Gln Ser Gly Arg Glu Leu Ile Asp Phe Ala
        35                  40                  45

Gly Gly Ile Ala Val Asn Val Leu Gly His Cys His Pro Ala Leu Val
    50                  55                  60

Ala Ala Leu Thr Glu Gln Ala Asn Thr Leu Trp His Ile Ser Asn Val
65                  70                  75                  80

```
Phe Thr Asn Glu Pro Thr Leu Arg Leu Gly Lys Lys Leu Val Asp Ala
             85                  90                  95
Thr Phe Ala Glu Arg Val Phe Phe Cys Asn Ser Gly Ala Glu Ala Asn
         100                 105                 110
Glu Ala Ala Phe Lys Leu Ala Arg Arg Val Ala His Asp Arg Phe Gly
     115                 120                 125
Pro Glu Lys His Glu Ile Ile Ala Ala Leu Asn Ser Phe His Gly Arg
 130                 135                 140
Thr Leu Phe Thr Val Ser Val Gly Gly Gln Pro Lys Tyr Ser Asp Gly
145                 150                 155                 160
Phe Gly Pro Lys Ile Gln Gly Ile Thr His Val Pro Tyr Asn Asp Leu
                 165                 170                 175
Glu Ala Leu Lys Ala Ala Ile Ser Asp Lys Thr Cys Ala Val Val Leu
             180                 185                 190
Glu Pro Ile Gln Gly Glu Gly Gly Val Leu Pro Ala Glu Lys Ala Tyr
         195                 200                 205
Leu Glu Gly Ala Arg Glu Leu Cys Asn Ala His Asn Ala Leu Leu Val
     210                 215                 220
Phe Asp Glu Val Gln Ser Gly Met Gly Arg Ser Gly Glu Leu Phe Ala
225                 230                 235                 240
Tyr Met His Tyr Gly Val Val Pro Asp Ile Leu Ser Ser Ala Lys Ser
                 245                 250                 255
Leu Gly Gly Gly Phe Pro Ile Ala Ala Met Leu Thr Thr Thr Asp Leu
             260                 265                 270
Ala Lys His Phe Thr Pro Gly Thr His Gly Thr Thr Tyr Gly Gly Asn
         275                 280                 285
Pro Leu Ala Cys Ala Val Gly Glu Ala Val Leu Asp Ile Val Asn Thr
     290                 295                 300
Arg Glu Thr Leu Asp Gly Val Lys Val Lys His Gln Gln Phe Lys Gln
305                 310                 315                 320
Arg Leu Glu Ala Leu Gly Lys Gln Phe Gly Leu Phe Glu Gln Val Arg
                 325                 330                 335
Gly Met Gly Leu Leu Leu Gly Cys Val Leu Asn Glu Ala Trp Lys Gly
             340                 345                 350
Lys Ala Lys Gln Val Leu Asp Ala Ala Ser Ala Glu Gly Leu Met Ile
         355                 360                 365
Leu Gln Ala Gly Pro Asp Val Val Arg Phe Ala Pro Ser Leu Val Val
     370                 375                 380
Glu Glu Arg Asp Ile Glu Gly Leu Ala Arg Phe Glu Arg Ala Leu
385                 390                 395                 400
                                                            Leu
Ser Lys Leu Ala Asn Ala
             405

<210> SEQ ID NO 10
<211> LENGTH: 1221
<212> TYPE: DNA
<213> ORGANISM: Pseudomonas putida

<400> SEQUENCE: 10
atgtccgttg agcaagcccc ggtgcaacgt gccgatttcg accaggtgat ggtccccaac    60
tattctccgg cggccttcat tcctgtgcga ggcgagggtt cccgcgtctg ggaccagtcg   120
ggtcgcgagt tgatcgactt tgccggcggc atcgcggtca atgccctggg ccactgccac   180
ccggcactgg tcaaggccct gactgaacag gccaacaccc tctggcacgt ctccaacgtg   240
```

-continued

```
ttcaccaacg agccggccct gcgcctggcc cacaagctgg tggacgccac ctttgccgac      300
cgcgcgttct tctgcaactc cggcgccgag tccaacgagg ccgctttcaa gctggcccgt      360
cgtgtggcgc atgaccgctt cggtccgcaa aagcacgaaa tcatcgccac cgtgaacagc      420
ttccacggtc gcaccctgtt taccgtcagc gtgggtggcc agccgaagta ctccgatggc      480
tttggcccga agatcaccgg tatcagccat gtgccgtaca acgacctgga agcgttgaag      540
gcacagattt ccgacaagac ctgcgccgtg gtgatcgagc cgatccaggg cgagagcggc      600
gtggttccgg ccgacaaggc ctacctggaa ggcgcgcgca agctgtgtga tgagcacaat      660
gcgctgctga tcttcgacga agtgcagact ggcgtgggcc gtaccggctc gctgtatgcc      720
taccagcact acggcgtgac cccggacatt ctgaccagtg ccaagagcct gggcggcggc      780
ttcccgattg cgccatgct gaccaccacc gagctggcca agcacctggc cgttggcacc      840
cacggcacca cctatggcgg caacccgctg ggttgcgccg tggcctgcgc ggtgctggat      900
gtggtcaaca ccccggaaac cctggccggt atcaaggcaa agcacgagcg cttcaaaacc      960
cgcctggagc agatcggcca gcagtacaac ctgttcagcc aggtgcgtgg cgtcggcttg     1020
ctgctgggct gtgtcttgac cgaggcctgg caaggcaagg ccaaggacgt gctcaatgct     1080
gccgagaaag aaggcgtgat ggtgctgcag gccggcccgg acgtggtccg cttcgcgcca     1140
agcctggtgg ttgaagatgc tgacatcgac gaaggcctgg accgcttcga acgcgctgtg     1200
gccacactga ccaaaggctg a                                               1221
```

<210> SEQ ID NO 11
<211> LENGTH: 406
<212> TYPE: PRT
<213> ORGANISM: Pseudomonas putida

<400> SEQUENCE: 11

```
Met Ser Val Glu Gln Ala Pro Val Gln Arg Ala Asp Phe Asp Gln Val
1               5                   10                  15

Met Val Pro Asn Tyr Ser Pro Ala Ala Phe Ile Pro Val Arg Gly Glu
            20                  25                  30

Gly Ser Arg Val Trp Asp Gln Ser Gly Arg Glu Leu Ile Asp Phe Ala
        35                  40                  45

Gly Gly Ile Ala Val Asn Ala Leu Gly His Cys His Pro Ala Leu Val
    50                  55                  60

Lys Ala Leu Thr Glu Gln Ala Asn Thr Leu Trp His Val Ser Asn Val
65                  70                  75                  80

Phe Thr Asn Glu Pro Ala Leu Arg Leu Ala His Lys Leu Val Asp Ala
                85                  90                  95

Thr Phe Ala Asp Arg Ala Phe Phe Cys Asn Ser Gly Ala Glu Ser Asn
            100                 105                 110

Glu Ala Ala Phe Lys Leu Ala Arg Arg Val Ala His Asp Arg Phe Gly
        115                 120                 125

Pro Gln Lys His Glu Ile Ile Ala Thr Val Asn Ser Phe His Gly Arg
    130                 135                 140

Thr Leu Phe Thr Val Ser Val Gly Gly Gln Pro Lys Tyr Ser Asp Gly
145                 150                 155                 160

Phe Gly Pro Lys Ile Thr Gly Ile Ser His Val Pro Tyr Asn Asp Leu
                165                 170                 175

Glu Ala Leu Lys Ala Gln Ile Ser Asp Lys Thr Cys Ala Val Val Ile
            180                 185                 190
```

| | | | | | | | | | | |
|---|---|---|---|---|---|---|---|---|---|---|
| Glu | Pro | Ile | Gln | Gly | Glu | Ser | Gly | Val | Val | Pro | Ala | Asp | Lys | Ala | Tyr |
| | | 195 | | | | 200 | | | | 205 | | | | | |

Glu Pro Ile Gln Gly Glu Ser Gly Val Val Pro Ala Asp Lys Ala Tyr
            195                 200                 205

Leu Glu Gly Ala Arg Lys Leu Cys Asp Glu His Asn Ala Leu Leu Ile
    210                 215                 220

Phe Asp Glu Val Gln Thr Gly Val Gly Arg Thr Gly Ser Leu Tyr Ala
225                 230                 235                 240

Tyr Gln His Tyr Gly Val Thr Pro Asp Ile Leu Thr Ser Ala Lys Ser
                245                 250                 255

Leu Gly Gly Gly Phe Pro Ile Gly Ala Met Leu Thr Thr Thr Glu Leu
            260                 265                 270

Ala Lys His Leu Ala Val Gly Thr His Gly Thr Thr Tyr Gly Gly Asn
    275                 280                 285

Pro Leu Gly Cys Ala Val Ala Cys Ala Val Leu Asp Val Val Asn Thr
290                 295                 300

Pro Glu Thr Leu Ala Gly Ile Lys Ala Lys His Glu Arg Phe Lys Thr
305                 310                 315                 320

Arg Leu Glu Gln Ile Gly Gln Gln Tyr Asn Leu Phe Ser Gln Val Arg
                325                 330                 335

Gly Val Gly Leu Leu Leu Gly Cys Val Leu Thr Glu Ala Trp Gln Gly
            340                 345                 350

Lys Ala Lys Asp Val Leu Asn Ala Ala Glu Lys Glu Gly Val Met Val
    355                 360                 365

Leu Gln Ala Gly Pro Asp Val Val Arg Phe Ala Pro Ser Leu Val Val
370                 375                 380

Glu Asp Ala Asp Ile Asp Glu Gly Leu Asp Arg Phe Glu Arg Ala Val
385                 390                 395                 400

Ala Thr Leu Thr Lys Gly
                405

<210> SEQ ID NO 12
<211> LENGTH: 1221
<212> TYPE: DNA
<213> ORGANISM: Pseudomonas resinovorans

<400> SEQUENCE: 12

```
atgtccgttg agcatgcgca ggtcgagcgc gccgatttcg acaaggtgat ggttcccaac       60
tatgccccccg ccgctttcat cccggtacgt ggcgaaggct cccgcgtctg ggaccaatcc      120
ggtcgcgagc tgatcgattt cgccggtggc atcgccgtga actccctggg ccatgcgcac      180
cccgcgctgg tcaaggcgct gaccgaacag gccaacaaga tctggcacgt atccaacgtt      240
ttcaccaacg agccggccct gcgcctggcc aagaagctgg tggacgccac cttcgccgag      300
cgggtgttcc tcgccaactc cggcgccgag gccaacgaag cggctttcaa actggcccgt      360
cgttatgccc atgacgtcta tgcccgcag aagcacgaga tcatttccgc caccaacagc      420
ttccacggtc gcaccctgtt caccgtgacc gttggcggcc agccgaaata ctccgacggc      480
ttcgggccga agatggaagg catcacccac gttgcctaca cgatctgga cgccctcaag      540
gcggccattt ccgacaagac ctgcgccgtg gtccttgagc ccgtgcaggg cgagggcggc      600
gtgctgccgg ccgacaaggc ctacctggaa ggcgcccgca gctgtgcga cgagcacaac      660
gcgctgctga tcttcgacga agtgcagagc ggcatgggcc gtaccggcca cttgttcgcc      720
tacgagcact acggcgtgac cccggacatc ctctccagtg ccaagagcct gggcggcggc      780
ttccccatcg gcgccatgct gaccaccacc gagatcgcca agcacctggc ggtgggcacc      840
cacggcacta cctacggcgg caacccgctg gcgagtgcgg tggccgaagc ggtactggac      900
```

-continued

```
gtgatcaaca ccccggaagt gctcagcggc atcaatgcca agcacgaccg cttcaaggcc      960
cgcctcgacg ccatcggcgc caagtacggc atcttcagtg aagtccgtgg cctgggcctg     1020
ctgatcggcg ccgtgctgac cgacgcctgg aagggcaagg ccaaggacgt gctgaacgcc     1080
gccgagaagg aggccgtgat ggtcctccag gccggtccgg acgtggtgcg cttcgcgccc     1140
agcctggtga ttccggatgc ggacatcgac gccggcctgg accgcttcga gcgcgccgtc     1200
gccaagctga cccaggcgta a                                                1221
```

<210> SEQ ID NO 13
<211> LENGTH: 406
<212> TYPE: PRT
<213> ORGANISM: Pseudomonas resinovorans
<400> SEQUENCE: 13

```
Met Ser Val Glu His Ala Gln Val Glu Arg Ala Asp Phe Asp Lys Val
1               5                   10                  15

Met Val Pro Asn Tyr Ala Pro Ala Ala Phe Ile Pro Val Arg Gly Glu
            20                  25                  30

Gly Ser Arg Val Trp Asp Gln Ser Gly Arg Glu Leu Ile Asp Phe Ala
        35                  40                  45

Gly Gly Ile Ala Val Asn Ser Leu Gly His Ala His Pro Ala Leu Val
    50                  55                  60

Lys Ala Leu Thr Glu Gln Ala Asn Lys Ile Trp His Val Ser Asn Val
65                  70                  75                  80

Phe Thr Asn Glu Pro Ala Leu Arg Leu Ala Lys Lys Leu Val Asp Ala
                85                  90                  95

Thr Phe Ala Glu Arg Val Phe Leu Ala Asn Ser Gly Ala Glu Ala Asn
            100                 105                 110

Glu Ala Ala Phe Lys Leu Ala Arg Arg Tyr Ala His Asp Val Tyr Gly
        115                 120                 125

Pro Gln Lys His Glu Ile Ile Ser Ala Thr Asn Ser Phe His Gly Arg
    130                 135                 140

Thr Leu Phe Thr Val Thr Val Gly Gly Gln Pro Lys Tyr Ser Asp Gly
145                 150                 155                 160

Phe Gly Pro Lys Met Glu Gly Ile Thr His Val Ala Tyr Asn Asp Leu
                165                 170                 175

Asp Ala Leu Lys Ala Ala Ile Ser Asp Lys Thr Cys Ala Val Val Leu
            180                 185                 190

Glu Pro Val Gln Gly Glu Gly Gly Val Leu Pro Ala Asp Lys Ala Tyr
        195                 200                 205

Leu Glu Gly Ala Arg Lys Leu Cys Asp Glu His Asn Ala Leu Leu Ile
    210                 215                 220

Phe Asp Glu Val Gln Ser Gly Met Gly Arg Thr Gly His Leu Phe Ala
225                 230                 235                 240

Tyr Glu His Tyr Gly Val Thr Pro Asp Ile Leu Ser Ser Ala Lys Ser
                245                 250                 255

Leu Gly Gly Gly Phe Pro Ile Gly Ala Met Leu Thr Thr Thr Glu Ile
            260                 265                 270

Ala Lys His Leu Ala Val Gly Thr His Gly Thr Thr Tyr Gly Gly Asn
        275                 280                 285

Pro Leu Ala Ser Ala Val Ala Glu Ala Val Leu Asp Val Ile Asn Thr
    290                 295                 300
```

```
Pro Glu Val Leu Ser Gly Ile Asn Ala Lys His Asp Arg Phe Lys Ala
305                 310                 315                 320

Arg Leu Asp Ala Ile Gly Ala Lys Tyr Gly Ile Phe Ser Glu Val Arg
                325                 330                 335

Gly Leu Gly Leu Leu Ile Gly Ala Val Leu Thr Asp Ala Trp Lys Gly
                340                 345                 350

Lys Ala Lys Asp Val Leu Asn Ala Ala Glu Lys Glu Ala Val Met Val
                355                 360                 365

Leu Gln Ala Gly Pro Asp Val Val Arg Phe Ala Pro Ser Leu Val Ile
        370                 375                 380

Pro Asp Ala Asp Ile Asp Ala Gly Leu Asp Arg Phe Glu Arg Ala Val
385                 390                 395                 400

Ala Lys Leu Thr Gln Ala
                405

<210> SEQ ID NO 14
<211> LENGTH: 1218
<212> TYPE: DNA
<213> ORGANISM: Pseudomonas syringae

<400> SEQUENCE: 14
```

| | | | | | |
|---|---|---|---|---|---|
| atgtccgttg | agcatgctgc | ggtgcaacgc | gccgatttcg | accaggtaat | ggtccccaat | 60 |
| tacgccccgg | ccgggttcat | ccctgtgcgc | ggtgcgggct | cccgggtctg | ggatcaggcg | 120 |
| gggcgcgaac | tggtggattt | ctcgggcggg | atcgccgtca | acgtattggg | ccactgccac | 180 |
| ccggcgctgg | tcgtgccctt | gaccgagcag | gccaataacc | tctggcatgt | gtccaacgtc | 240 |
| ttcaccaacg | agccgaccct | gcgcctggcg | aaaaaactgg | tggatgcgac | gttcgccgag | 300 |
| cgcgtgttct | tctgtaactc | cggtgcggaa | gccaacgaag | ccgccttcaa | gctggcacgt | 360 |
| cgtgtggcgc | atgaccagta | cggcccggaa | aagtacgaaa | tcatcgcggc | gctgaacagt | 420 |
| tttcatggcc | gtaccctgtt | caccgtcagc | gtcggtgggc | agccgaagta | ctccgatggt | 480 |
| ttcgggccga | agatcaccgg | catcagccat | gtgccgtaca | cgacctcga | cgcactgaag | 540 |
| gccgctgtga | ccgacaagac | ctgtgccgtg | gtgctggagc | cgatccaggg | cgagggcggt | 600 |
| gttctgccgg | gtcagctgga | atacctgcaa | ggtgcgcgca | aactgtgtga | cgagcacaac | 660 |
| gccctgctgg | tgttcgatga | agtgcagagc | ggcatgggcc | gtagcggtca | tctgttcgcc | 720 |
| tacatgcatt | acggcgtgac | cccggacatc | cttttccagcg | ccaagagcat | cggcggaggt | 780 |
| ttcccgctgg | cggcgatgtt | gaccactgaa | aagctcgcca | ggcactttgc | ggtcggcgtt | 840 |
| cacggcacca | cctatggcgg | caacccgctg | cgtgtgcgg | tcggtgaggc | ggtgatcgac | 900 |
| gtgatcaata | cgcctgaagt | gctggctggc | gtacagcgca | agcatcagca | gttcaagacc | 960 |
| cgtctgcaaa | gcattggcca | gcaatacggc | gtgttcagcg | aagtgcgcgg | tctgggtctg | 1020 |
| ctgatcggtt | gcgtgttgtc | cgatgcctgg | aagggcaagg | ccaaggacat | cttcaatgcg | 1080 |
| gccgaggctc | aggacctgat | gatcctgcag | gccggccctg | acgtgattcg | tttcgcgccg | 1140 |
| agcctggtga | ttgaagacgc | ggacatcgaa | gagggcctga | accgctttga | acgcgccatc | 1200 |
| gcccaactga | catcctga   |            |            |            |            | 1218 |

```
<210> SEQ ID NO 15
<211> LENGTH: 405
<212> TYPE: PRT
<213> ORGANISM: Pseudomonas syringae
```

<400> SEQUENCE: 15

```
Met Ser Val Glu His Ala Ala Val Gln Arg Ala Asp Phe Asp Gln Val
1               5                   10                  15

Met Val Pro Asn Tyr Ala Pro Ala Gly Phe Ile Pro Val Arg Gly Ala
            20                  25                  30

Gly Ser Arg Val Trp Asp Gln Ala Gly Arg Glu Leu Val Asp Phe Ser
        35                  40                  45

Gly Gly Ile Ala Val Asn Val Leu Gly His Cys His Pro Ala Leu Val
    50                  55                  60

Gly Ala Leu Thr Glu Gln Ala Asn Asn Leu Trp His Val Ser Asn Val
65                  70                  75                  80

Phe Thr Asn Glu Pro Thr Leu Arg Leu Ala Lys Lys Leu Val Asp Ala
                85                  90                  95

Thr Phe Ala Glu Arg Val Phe Phe Cys Asn Ser Gly Ala Glu Ala Asn
            100                 105                 110

Glu Ala Ala Phe Lys Leu Ala Arg Arg Val Ala His Asp Gln Tyr Gly
        115                 120                 125

Pro Glu Lys Tyr Glu Ile Ile Ala Ala Leu Asn Ser Phe His Gly Arg
    130                 135                 140

Thr Leu Phe Thr Val Ser Val Gly Gly Gln Pro Lys Tyr Ser Asp Gly
145                 150                 155                 160

Phe Gly Pro Lys Ile Thr Gly Ile Ser His Val Pro Tyr Asn Asp Leu
                165                 170                 175

Asp Ala Leu Lys Ala Ala Val Thr Asp Lys Thr Cys Ala Val Val Leu
            180                 185                 190

Glu Pro Ile Gln Gly Glu Gly Val Leu Pro Gly Gln Leu Glu Tyr
        195                 200                 205

Leu Gln Gly Ala Arg Lys Leu Cys Asp Glu His Asn Ala Leu Leu Val
    210                 215                 220

Phe Asp Glu Val Gln Ser Gly Met Gly Arg Ser Gly His Leu Phe Ala
225                 230                 235                 240

Tyr Met His Tyr Gly Val Thr Pro Asp Ile Leu Ser Ser Ala Lys Ser
                245                 250                 255

Ile Gly Gly Gly Phe Pro Leu Ala Ala Met Leu Thr Thr Glu Lys Leu
            260                 265                 270

Ala Arg His Phe Ala Val Gly Val His Gly Thr Thr Tyr Gly Gly Asn
        275                 280                 285

Pro Leu Ala Cys Ala Val Gly Glu Ala Val Ile Asp Val Ile Asn Thr
    290                 295                 300

Pro Glu Val Leu Ala Gly Val Gln Arg Lys His Gln Gln Phe Lys Thr
305                 310                 315                 320

Arg Leu Gln Ser Ile Gly Gln Gln Tyr Gly Val Phe Ser Glu Val Arg
                325                 330                 335

Gly Leu Gly Leu Leu Ile Gly Cys Val Leu Ser Asp Ala Trp Lys Gly
            340                 345                 350

Lys Ala Lys Asp Ile Phe Asn Ala Ala Glu Ala Gln Asp Leu Met Ile
        355                 360                 365

Leu Gln Ala Gly Pro Asp Val Ile Arg Phe Ala Pro Ser Leu Val Ile
    370                 375                 380

Glu Asp Ala Asp Ile Glu Glu Gly Leu Asn Arg Phe Glu Arg Ala Ile
385                 390                 395                 400

Ala Gln Leu Thr Ser
            405
```

<210> SEQ ID NO 16
<211> LENGTH: 1218
<212> TYPE: DNA
<213> ORGANISM: Pseudomonas thermotolerans

<400> SEQUENCE: 16

```
atgtccgttc agcacgaacc ggtgcagcgc gccgatttcg accaatacat ggtgcccaac      60
tatgcacccg ccgccttcat tccggtgcgt ggcgagggct cgcgcgtctg ggaccagagc     120
ggtcgagagc tgatcgactt cgccggcggc atcgccgtga actccctggg ccacgcgcat     180
ccggcgctgg tcaaggcact caccgagcag gccggcaaga tctggcacgt ttccaacgtg     240
ttcaccaacg agccggccct cgcgcttggc aagaagctgg tcggcgccac cttcgccgag     300
cgggtgttcc tcgccaactc cggcgccgag gccaacgagg cggccttcaa gctggcccgc     360
cgctacgcca cgacgtcta cggtcccgag aagtacgaga tcatcgccgc cagcaacagt     420
tttcacggcc gtaccctgtt caccgtcaac gtcggcggcc agcccaagta ttccgacggc     480
tcgggccga agatcgaggg catcacccac gtccccctaca cgacctgga ggccctcaag     540
gcggtcattt ccgccaagac ctgcgcggtg gtcctcgagc cggtacaggg cgagggcggc     600
gtgttgccgg ccgatcaggc ctacctggag ggcgtgcgcg agctgtgcaa ccagcacaac     660
gcgctgctgg tgttcgacga ggtgcagagt ggcatgggcc gtaccggcga gctgttcgcc     720
tacatgcact acggggtgac tccggacatc ctgtccagcg ccaagagcct gggcggtggc     780
ttcccgatcg gcgccatgat gaccaccagc gagatcgcca agcacctgtc ggtgggcacc     840
cacggcacca cctacggcgg caacccgctg gcctgcgcgg tggccggggc ggtgttcgac     900
gtgatcaaca gccgcgaggt gctcgacggg gtcaagtcca agcaccagcg cttcaaggcc     960
cgcctccagg agatgggcgc caagtacggc atcttcagcg aggtgcgcgg cctcggcctg    1020
ctgatcggcg cgcagttgag cgagacctgg aagggcaagg cccgcgacgt gctcaacgcc    1080
gccgagcagg aggcgctgat ggtccttcag gccggtccgg acgtggtgcg cttcgcgccc    1140
agcctggtga tcccggacgc cgatatcgac gagggtctcg agcgtctcga gcgggctatc    1200
gtcaagctga cccggtag                                                   1218
```

<210> SEQ ID NO 17
<211> LENGTH: 405
<212> TYPE: PRT
<213> ORGANISM: Pseudomonas thermotolerans

<400> SEQUENCE: 17

```
Met Ser Val Gln His Glu Pro Val Gln Arg Ala Asp Phe Asp Gln Tyr
1               5                   10                  15

Met Val Pro Asn Tyr Ala Pro Ala Ala Phe Ile Pro Val Arg Gly Glu
            20                  25                  30

Gly Ser Arg Val Trp Asp Gln Ser Gly Arg Glu Leu Ile Asp Phe Ala
        35                  40                  45

Gly Gly Ile Ala Val Asn Ser Leu Gly His Ala His Pro Ala Leu Val
    50                  55                  60

Lys Ala Leu Thr Glu Gln Ala Gly Lys Ile Trp His Val Ser Asn Val
65                  70                  75                  80

Phe Thr Asn Glu Pro Ala Leu Arg Leu Ala Lys Lys Leu Val Gly Ala
                85                  90                  95

Thr Phe Ala Glu Arg Val Phe Leu Ala Asn Ser Gly Ala Glu Ala Asn
            100                 105                 110
```

```
Glu Ala Ala Phe Lys Leu Ala Arg Arg Tyr Ala Asn Asp Val Tyr Gly
            115                 120                 125
Pro Glu Lys Tyr Glu Ile Ile Ala Ala Ser Asn Ser Phe His Gly Arg
        130                 135                 140
Thr Leu Phe Thr Val Asn Val Gly Gly Gln Pro Lys Tyr Ser Asp Gly
145                 150                 155                 160
Phe Gly Pro Lys Ile Glu Gly Ile Thr His Val Pro Tyr Asn Asp Leu
                165                 170                 175
Glu Ala Leu Lys Ala Val Ile Ser Ala Lys Thr Cys Ala Val Val Leu
            180                 185                 190
Glu Pro Val Gln Gly Glu Gly Gly Val Leu Pro Ala Asp Gln Ala Tyr
        195                 200                 205
Leu Glu Gly Val Arg Glu Leu Cys Asn Gln His Asn Ala Leu Leu Val
210                 215                 220
Phe Asp Glu Val Gln Ser Gly Met Gly Arg Thr Gly Glu Leu Phe Ala
225                 230                 235                 240
Tyr Met His Tyr Gly Val Thr Pro Asp Ile Leu Ser Ser Ala Lys Ser
                245                 250                 255
Leu Gly Gly Gly Phe Pro Ile Gly Ala Met Met Thr Thr Ser Glu Ile
            260                 265                 270
Ala Lys His Leu Ser Val Gly Thr His Gly Thr Thr Tyr Gly Gly Asn
        275                 280                 285
Pro Leu Ala Cys Ala Val Ala Gly Ala Val Phe Asp Val Ile Asn Ser
290                 295                 300
Arg Glu Val Leu Asp Gly Val Lys Ser Lys His Gln Arg Phe Lys Ala
305                 310                 315                 320
Arg Leu Gln Glu Met Gly Ala Lys Tyr Gly Ile Phe Ser Glu Val Arg
                325                 330                 335
Gly Leu Gly Leu Leu Ile Gly Ala Gln Leu Ser Glu Thr Trp Lys Gly
            340                 345                 350
Lys Ala Arg Asp Val Leu Asn Ala Ala Glu Gln Glu Ala Leu Met Val
        355                 360                 365
Leu Gln Ala Gly Pro Asp Val Val Arg Phe Ala Pro Ser Leu Val Ile
370                 375                 380
Pro Asp Ala Asp Ile Asp Glu Gly Leu Glu Arg Leu Glu Arg Ala Ile
385                 390                 395                 400
Val Lys Leu Thr Arg
                405

<210> SEQ ID NO 18
<211> LENGTH: 20
<212> TYPE: DNA
<213> ORGANISM: Artificial Sequence
<220> FEATURE:
<223> OTHER INFORMATION: primer 27F

<400> SEQUENCE: 18
agagtttgat cctggctcag                                              20

<210> SEQ ID NO 19
<211> LENGTH: 19
<212> TYPE: DNA
<213> ORGANISM: Artificial Sequence
<220> FEATURE:
<223> OTHER INFORMATION: primer 1492R
```

<400> SEQUENCE: 19
ggttaccttg ttacgactt                                                        19

<210> SEQ ID NO 20
<211> LENGTH: 22
<212> TYPE: DNA
<213> ORGANISM: Artificial Sequence
<220> FEATURE:
<223> OTHER INFORMATION: primer NCPPB 5P

<400> SEQUENCE: 20
atgagcaaga ctaacgaatc cc                                                    22

<210> SEQ ID NO 21
<211> LENGTH: 20
<212> TYPE: DNA
<213> ORGANISM: Artificial Sequence
<220> FEATURE:
<223> OTHER INFORMATION: primer NCPPB 3P

<400> SEQUENCE: 21
tccagaatgg ccagcccgcg                                                       20

<210> SEQ ID NO 22
<211> LENGTH: 32
<212> TYPE: DNA
<213> ORGANISM: Artificial Sequence
<220> FEATURE:
<223> OTHER INFORMATION: primer argD F2

<400> SEQUENCE: 22
atttaaggat ccgtccgccc cgcacacccc gg                                         32

<210> SEQ ID NO 23
<211> LENGTH: 31
<212> TYPE: DNA
<213> ORGANISM: Artificial Sequence
<220> FEATURE:
<223> OTHER INFORMATION: primer argD R2

<400> SEQUENCE: 23
atttaagagc tctcaggcct gggtcagcgt c                                          31

<210> SEQ ID NO 24
<211> LENGTH: 35
<212> TYPE: DNA
<213> ORGANISM: Artificial Sequence
<220> FEATURE:
<223> OTHER INFORMATION: primer gabT F

<400> SEQUENCE: 24
atttaacata tgcaacgccg tgtcgccgcc gttcc                                      35

<210> SEQ ID NO 25
<211> LENGTH: 35
<212> TYPE: DNA
<213> ORGANISM: Artificial Sequence
<220> FEATURE:
<223> OTHER INFORMATION: primer gabT R

<400> SEQUENCE: 25
atttaagaat tctcaggtca gctcgtcgaa acact                                      35